United States Patent
Gougoutas

(10) Patent No.: US 6,774,112 B2
(45) Date of Patent: Aug. 10, 2004

(54) AMINO ACID COMPLEXES OF C-ARYL GLUCOSIDES FOR TREATMENT OF DIABETES AND METHOD

(75) Inventor: Jack Z. Gougoutas, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/117,914

(22) Filed: Apr. 8, 2002

(65) Prior Publication Data

US 2003/0064935 A1 Apr. 3, 2003

Related U.S. Application Data

(60) Provisional application No. 60/283,097, filed on Apr. 11, 2001.

(51) Int. Cl.[7] ............................. A61K 31/70; C07H 5/06
(52) U.S. Cl. ............................. 514/23; 514/4; 514/866; 536/1.11; 536/17.4; 536/17.6; 536/18.4
(58) Field of Search ............................. 514/4, 23, 866; 536/1.11, 17.4, 17.6, 18.4

(56) References Cited

U.S. PATENT DOCUMENTS

| | | |
|---|---|---|
| 3,674,836 A | 7/1972 | Creger |
| 3,983,140 A | 9/1976 | Endo et al. |
| 4,027,009 A | 5/1977 | Grier et al. |
| 4,231,938 A | 11/1980 | Monaghan et al. |
| 4,346,227 A | 8/1982 | Terahara et al. |

(List continued on next page.)

FOREIGN PATENT DOCUMENTS

| | | |
|---|---|---|
| EP | 0221025 | 10/1986 |
| FR | 2596393 | 4/1986 |
| GB | 2205837 | 12/1988 |
| WO | WO 86/03488 | 6/1986 |
| WO | WO 86/07054 | 12/1986 |

(List continued on next page.)

OTHER PUBLICATIONS

Johannsson et al., J. Clin. Endocrinol. Metab., 82:727–34 (1997).
Benhaddou et al., Carbohydr. Res., 260:243–250 (1994).
Murakami et al., Diabetes 47:1841–1847 (1998).
Hughes et al., Biochemistry, 38(36):11597–11603 (1999).
Yamada et al., Bioorg. & Med. Chem. Lett., 8:1537–1540 (1998).
Ashworth et al., Bioorg. & Med. Chem. Lett., 6:1163–1166 (1996).
Ashworth et al., Bioorg. & Med. Chem. Lett., 6:2745–2748 (1996).
Biller et al., J. Med. Chem., 31(10):1869–1871 (1988).
Biller et al., Current Pharmaceutical Design, 2:1–40 (1996).
Ortiz De Montellano et al., J. Med. Chem., 20:243–249 (1977).
Corey et al., J. Am. Chem. Soc., 98:1291–1293 (1976).
McClard et al., J. Am. Chem. Soc., 109:5544–5545 (1987).
Sorbera et al., Drugs of the Future, 24:9–15 (1999).
Nicolosi et al., Atherosclerosis, 137(1):77–85 (1998).
Ghiselli, Cardiovasc. Drug Rev., 16(1):16–30 (1998).
Smith et al., Bioorg. Med. Chem. Lett., 6(1):47–50 (1996).
Krause et al., Inflammation: Mediators Pathways, Publisher: CRC, Boca Raton, Fla., p. 173–98 (1995).
Sliskovic et al., Curr. Med. Chem. 1(3):204–25 (1994).

(List continued on next page.)

*Primary Examiner*—James O. Wilson
*Assistant Examiner*—Devesh Khare
(74) *Attorney, Agent, or Firm*—Jonathan N. Provoost; Mary Vanatten; Maureen P. O'Brien

(57) ABSTRACT

Crystalline complexes are obtained from a 1:1 or 2:1 mixtures of either the (D) or (L) enantiomer of natural amino acids and compounds of formula

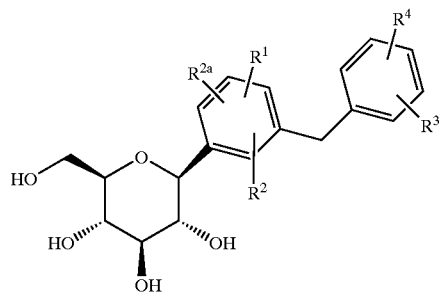

wherein
$R^1$, $R^2$ and $R^{2a}$ are independently hydrogen, OH, $OR^5$, alkyl, —$OCHF_2$, —$OCF_3$, —$SR^{5a}$ or halogen;
$R^3$ and $R^4$ are independently hydrogen, OH, $OR^{5b}$, alkyl, cycloalkyl, $CF_3$, —$OCHF_2$, —$OCF_3$, halogen, —$CONR^6R^{6a}$, —$CO_2R^{5c}$, —$CO_2H$, —$COR^{6b}$, —CH(OH)$R^{6c}$, —CH($OR^{5d}$)$R^{6d}$, —CN, —$NHCOR^{5e}$, —$NHSO_2R^{5f}$, —$NHSO_2$Aryl, —$SR^{5g}$, —$SOR^{5h}$, —$SO_2R^{5i}$, or a five, six or seven membered heterocycle which may contain 1 to 4 heteroatoms in the ring which are N, O, S, SO, and/or $SO_2$, or $R^3$ and $R^4$ together with the carbons to which they are attached form an annelated five, six or seven membered carbocycle or heterocycle which may contain 1 to 4 heteroatoms in the ring which are N, O, S, SO, and/or $SO_2$;
$R^5$, $R^{5a}$, $R^{5b}$, $R^{5c}$, $R^{5d}$, $R^{5e}$, $R^{5f}$, $R^{5g}$, $R^{5h}$ and $R^{5i}$ are independently alkyl;
$R^6$, $R^{6a}$, $R^{6b}$, $R^{6c}$ and $R^{6d}$ are independently hydrogen, alkyl, aryl, alkylaryl or cycloalkyl, or $R^6$ and $R^{6a}$ together with the nitrogen to which they are attached form an annelated five, six or seven membered heterocycle which may contain 1 to 4 heteroatoms in the ring which are N, O, S, SO, and/or $SO_2$.

A method is also provided for treating diabetes and related diseases employing an SGLT2 inhibiting amount of the above complex alone or in combination with another antidiabetic agent or other therapeutic agent.

19 Claims, 4 Drawing Sheets

U.S. PATENT DOCUMENTS

| | | |
|---|---|---|
| 4,448,784 A | 5/1984 | Glamkowski et al. |
| 4,450,171 A | 5/1984 | Hoffman et al. |
| 4,499,289 A | 2/1985 | Baran et al. |
| 4,572,912 A | 2/1986 | Yoshioka et al. |
| 4,613,610 A | 9/1986 | Wareing |
| 4,639,436 A | 1/1987 | Junge et al. |
| 4,647,576 A | 3/1987 | Hoefle et al. |
| 4,681,893 A | 7/1987 | Roth |
| 4,686,237 A | 8/1987 | Anderson |
| 4,759,923 A | 7/1988 | Buntin et al. |
| 4,871,721 A | 10/1989 | Biller |
| 4,904,769 A | 2/1990 | Rauenbusch |
| 4,924,024 A | 5/1990 | Biller |
| 5,006,530 A | 4/1991 | Angerbauer et al. |
| 5,011,930 A | 4/1991 | Fujikawa et al. |
| 5,177,080 A | 1/1993 | Angerbauer et al. |
| 5,260,440 A | 11/1993 | Hirai et al. |
| 5,273,995 A | 12/1993 | Roth |
| 5,346,701 A | 9/1994 | Heiber et al. |
| 5,354,772 A | 10/1994 | Kathawala |
| 5,385,929 A | 1/1995 | Bjorge et al. |
| 5,444,050 A | 8/1995 | Kogan et al. |
| 5,488,064 A | 1/1996 | Sher |
| 5,491,134 A | 2/1996 | Sher |
| 5,506,219 A | 4/1996 | Robl |
| 5,541,204 A | 7/1996 | Sher et al. |
| 5,594,016 A | 1/1997 | Ueno et al. |
| 5,595,872 A | 1/1997 | Wetterau, II et al. |
| 5,614,492 A | 3/1997 | Habener |
| 5,631,224 A | 5/1997 | Efendic et al. |
| 5,663,377 A | 9/1997 | Curley et al. |
| 5,686,104 A | 11/1997 | Mills et al. |
| 5,691,322 A | 11/1997 | Robl |
| 5,712,279 A | 1/1998 | Biller et al. |
| 5,712,396 A | 1/1998 | Magnin et al. |
| 5,739,135 A | 4/1998 | Biller et al. |
| 5,753,675 A | 5/1998 | Wattanasin |
| 5,760,246 A | 6/1998 | Biller et al. |
| 5,770,615 A | 6/1998 | Cheng et al. |
| 5,776,983 A | 7/1998 | Washburn et al. |
| 5,827,875 A | 10/1998 | Dickson, Jr. et al. |
| 5,885,983 A | 3/1999 | Biller et al. |
| 5,962,440 A | 10/1999 | Sulsky et al. |
| 6,414,126 B1 * | 7/2002 | Ellsworth et al. ........... 536/17.2 |
| 6,515,117 B2 * | 2/2003 | Ellsworth et al. ........... 536/17.2 |

FOREIGN PATENT DOCUMENTS

| | | |
|---|---|---|
| WO | WO 96/38144 | 12/1996 |
| WO | WO 97/12613 | 4/1997 |
| WO | WO 97/12615 | 4/1997 |
| WO | WO 97/21993 | 6/1997 |
| WO | WO98/31697 | 7/1998 |
| WO | WO 99/00353 | 1/1999 |
| WO | WO 99/38501 | 8/1999 |
| WO | WO 99/46272 | 9/1999 |
| WO | WO 99/61431 | 12/1999 |
| WO | WO 99/67278 | 12/1999 |
| WO | WO 99/67279 | 12/1999 |
| WO | WO01/16147 | 8/2001 |

OTHER PUBLICATIONS

Cornicelli et al., Current Pharmaceutical Design, 5:11–20 (1999).

Capson, PhD Dissertation, Jun., 1987, Dept. Med. Chem., U of Utah, pp16,17,40–43,48–51.

Stout et al., Chemtracts– Org. Chem., 8(6):359–62 (1995).

Salisbury et al., Atherosclerosis, 115:45–63 (1995).

Rosenblum et al., J. Med. Chem., 41:973–980 (1998).

Hara, Drugs of the Future, 24:425–430 (1999).

Sendobry et al., Brit. J. Pharmacology 120:1199–1206 (1997).

* cited by examiner

Structure of the 1:1 complex of compound 1 and L-phenylalanine described in Example 1

Structure of the 1:2 complex of Compound 3 and L-phenylalanine described in Example 4

Structure of the 1:2 complex of Compound 3 and L-proline described in Example 5. The dashed circle represents a disorded solvent site which may contain water, ethanol or methanol.

Structure of the 1:1 complex of Compound 3 and L-proline described in Example 6

AMINO ACID COMPLEXES OF C-ARYL GLUCOSIDES FOR TREATMENT OF DIABETES AND METHOD

This application claims priority from U.S. Provisional Application Serial No. 60/283,097 filed Apr. 11, 2001.

FIELD OF THE INVENTION

The present invention relates to the generation of crystalline amino acid complexes from amorphous C-aryl glucosides which are useful for the treatment of diabetes, especially type II diabetes, as well as hyperglycemia, hyperinsulinemia, obesity, hypertriglyceridemia, Syndrome X, diabetic complications, atherosclerosis and related diseases.

BACKGROUND OF THE INVENTION

Approximately 100 million people worldwide suffer from type II diabetes (NIDDM), which is characterized by hyperglycemia due to excessive hepatic glucose production and peripheral insulin resistance, the root causes for which are as yet unknown. Hyperglycemia is considered to be the major risk factor for the development of diabetic complications, and is likely to contribute directly to the impairment of insulin secretion seen in advanced NIDDM. Normalization of plasma glucose in NIDDM patients would be predicted to improve insulin action, and to offset the development of diabetic complications. An inhibitor of the sodium-dependent glucose transporter SGLT2 in the kidney is expected to aid in the normalization of plasma glucose levels, and perhaps body weight, by enhancing glucose excretion.

Hyperglycemia is a hallmark of type II diabetes (NIDDM); consistent control of plasma glucose levels in diabetes can offset the development of diabetic complications and beta cell failure seen in advanced disease. Plasma glucose is normally filtered in the kidney in the glomerulus and actively reabsorbed in the proximal tubule. SGLT2 appears to be the major transporter responsible for the reuptake of glucose at this site. The O-glucoside SGLT specific inhibitor phlorizin or closely related analogs inhibit this reuptake process in diabetic rodents and dogs resulting in normalization of plasma glucose levels by promoting glucose excretion without hypoglycemic side effects. Long term (6 month) treatment of Zucker diabetic rats with an O-glucoside SGLT2 inhibitor has been reported to improve insulin response to glycemia, improve insulin sensitivity, and delay the onset of nephropathy and neuropathy in these animals, with no detectable pathology in the kidney and no electrolyte imbalance in plasma. Selective inhibition of SGLT2 in diabetic patients would be expected to normalize plasma glucose by enhancing the excretion of glucose in the urine, thereby improving insulin sensitivity, and delaying the development of diabetic complications.

The present invention relates to C-aryl glucosides which are inhibitors of sodium dependent glucose transporters found in the intestine and kidney (SGLT2) and to a method for treating diabetes, especially type II diabetes, as well as hyperglycemia, hyperinsulinemia, obesity, hypertriglyceridemia, Syndrome X, diabetic complications, atherosclerosis and related diseases, employing such C-aryl glucosides alone or in combination with one, two or more other type antidiabetic agent and/or one, two or more other type therapeutic agents such as hypolipidemic agents.

DESCRIPTION OF THE DRAWINGS

With respect to the attached figures, only oxygen (O) and hydrogen (H) atoms of the neighboring molecules involved in H bonds (illustrated as dashed bonds) are shown. The remainder of the neighboring molecule is truncated.

Distances are given in Angstroms and represent to O—O or O—N interatomic distances.

DESCRIPTION OF THE INVENTION

Figure 1:
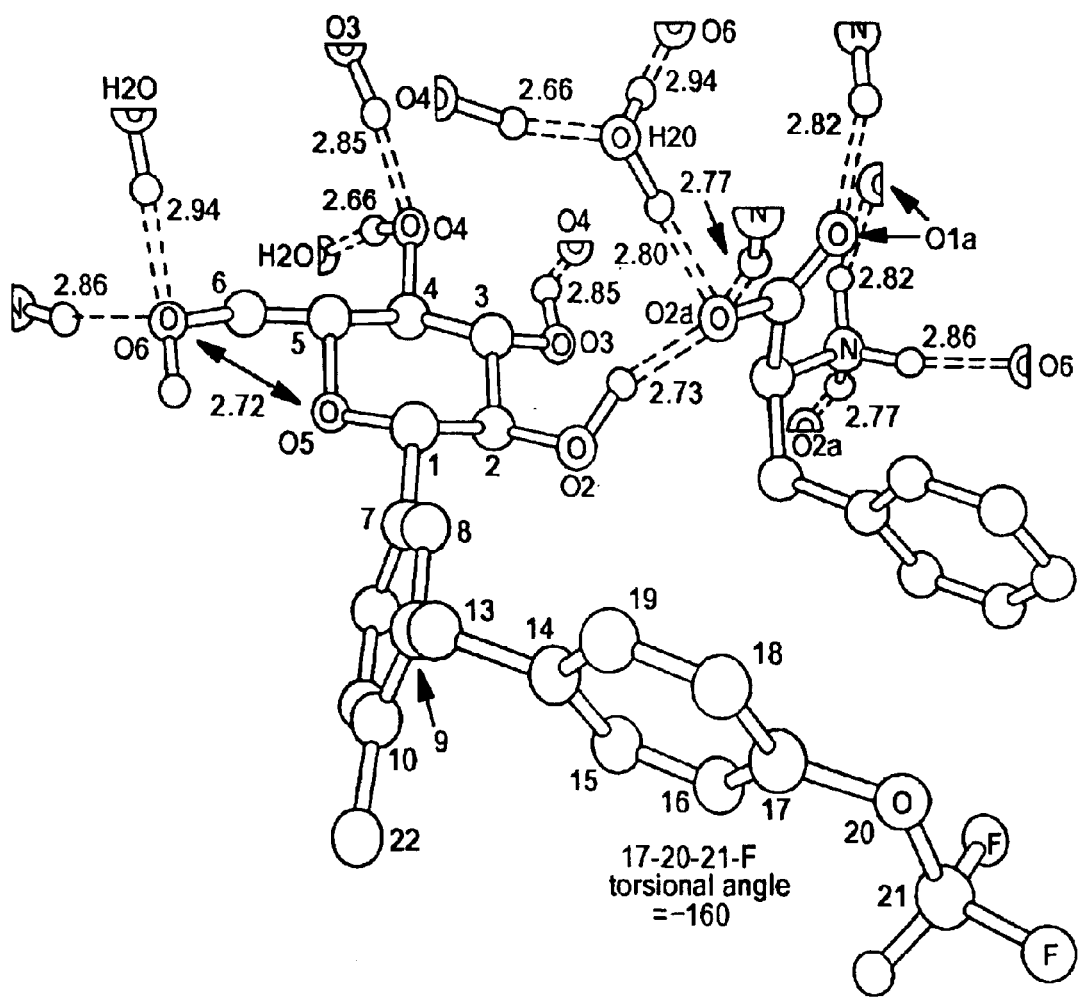
FIG. 1 represents the structure of the 1:1 complex of Compound 1 and L-phenylaline described in Example 1.

The instant invention provides a process for producing crystalline 2:1 or 1:1 complexes between either the (D) or (L) enantiomer of natural amino acids and amorphous C-aryl glucoside compounds of formula I

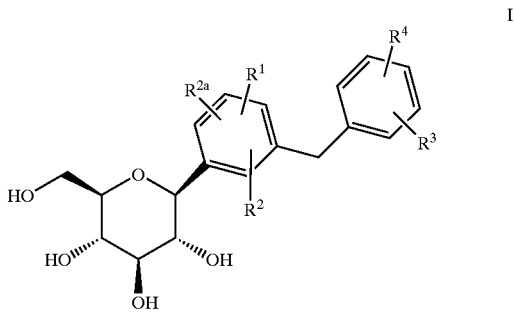

wherein $R^1$, $R^2$ and $R^{2a}$ are independently hydrogen, OH, $OR^5$, alkyl, $-OCHF_2$, $-OCF_3$, $-SR^{5a}$ or halogen;

$R^3$ and $R^4$ are independently hydrogen, OH, $OR^{5b}$, alkyl, cycloalkyl, $CF_3$, $-OCHF_2$, $-OCF_3$, halogen, $-CONR^6R^{6a}$, $-CO_2R^{5c}$, $-CO_2H$, $-COR^{6b}$, $-CH(OH)R^{6c}$, $-CH(OR^{5d})R^{6d}$, $-CN$, $-NHCOR^{5e}$, $-NHSO_2R^{5f}$, $-NHSO_2Aryl$, $-SR^{5g}$, $-SOR^{5h}$, $-SO_2R^{5i}$, $-SO_2Aryl$, or a five, six or seven membered heterocycle which may contain 1 to 4 heteroatoms in the ring which are N, O, S, SO, and/or $SO_2$, or $R^3$ and $R^4$ together with the carbons to which they are attached form an annelated five, six or seven membered carbocycle or heterocycle which may contain 1 to 4 heteroatoms in the ring which are N, O, S, SO, and/or $SO_2$;

$R^5$, $R^{5a}$, $R^{5b}$, $R^{5c}$, $R^{5d}$, $R^{5e}$, $R^{5f}$, $R^{5g}$, $R^{5h}$ and $R^{5i}$ are independently alkyl;

$R^6$, $R^{6a}$, $R^{6b}$, $R^{6c}$ and $R^{5d}$ are independently hydrogen, alkyl, aryl, alkylaryl or cycloalkyl, or $R^6$ and $R^{6a}$ together with the nitrogen to which they are attached form an annelated five, six or seven membered heterocycle which may contain 1 to 4 heteroatoms in the ring which are N, O, S, SO, and/or $SO_2$.

The compounds of formula I, as described in U.S. application Ser. No. 09/679,027, now U.S. Pat. No. 6,414,126, incorporated herein by reference, possess activity as inhibitors of the sodium dependent glucose transporters found in the intestine and kidney of mammals and are useful in the treatment of diabetes and the micro- and macrovascular complications of diabetes such as retinopathy, neuropathy, nephropathy, and wound healing.

The instant invention provides a means to convert compounds of formula I from viscous oils and amorphous solids to tractible crystalline solids that can be 1) conveniently isolated and transferred, 2) recrystallized to constant reproducible purity, and 3) formulated to provide pharmaceutical compositions that can be administered as tablets or in solution for treating or delaying the progression or onset of diabetes, especially type I and type II diabetes, including complications of diabetes, including retinopathy, neuropathy, nephropathy and delayed wound healing, and related diseases such as insulin resistance (impaired glucose homeostasis), hyperglycemia, hyperinsulinemia, elevated blood levels of fatty acids or glycerol, obesity, hyperlipidemia including hypertriglyceridemia, Syndrome X, atherosclerosis and hypertension, and for increasing high density lipoprotein levels, wherein a therapeutically effective amount of a compound of formula I as an amino acid complex is administered to a human patient in need of treatment.

In addition, in accordance with the present invention, a method is provided for treating diabetes and related diseases as defined above and hereinafter, wherein a therapeutically effective amount of a combination of a complex of either the (D) or (L) enantiomer of natural amino acids with a compound of formula I and another type of antidiabetic agent and/or another type of therapeutic agent such as a hypolipidemic agent is administered to a human patient in need of treatment.

The conditions, diseases, and maladies collectively referred to as "Syndrome X" (also known as Metabolic Syndrome) are detailed in Johannsson *J. Clin. Endocrinol. Metab.*, 82, 727–34 (1997).

The term "other type of therapeutic agents" as employed herein refers to one or more antidiabetic agents (other than SGLT2 inhibitors of formula I), one or more anti-obesity agents, anti-hypertensive agents, anti-platelet agents, anti-atherosclerotic agents and/or one or more lipid-lowering agents (including anti-atherosclerosis agents).

In the above method of the invention, the amino acid complex of compound of formula I of the invention will be employed in a weight ratio to the one, two or more antidiabetic agent and/or one, two or more other type therapeutic agent (depending upon its mode of operation) within the range from about 0.01:1 to about 300:1, preferably from about 0.1:1 to about 10:1.

Preferred are compounds of formula IA

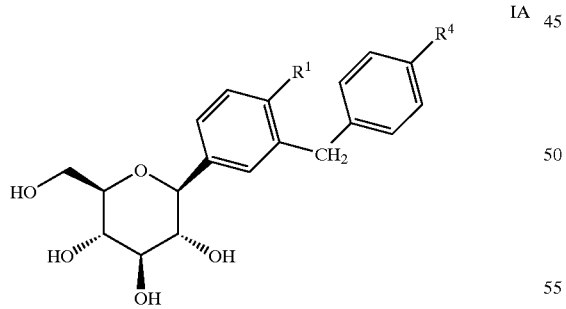

where $R^1$ is hydrogen, halogen, lower alkoxy, or lower alkyl and $R^4$ is lower alkyl, $R^{5a}O$, —$OCHF_2$, —$SR^{5g}$, —$SOR^{5h}$, —$SO_2R^{5i}$, or OH. It is preferred that $R^1$ be linked para to the glucoside bond and the $R^4$ substituent be linked at the para position.

DETAILED DESCRIPTION OF THE INVENTION

The amino acid complexes of compounds of formula I of the invention can be prepared by the following description wherein temperatures are expressed in degrees Centigrade.

A compound of formula I is dissolved in a water miscible solvent such as ethanol, 1-propanol, methanol that is heated to 50–80°. The solution is transferred rapidly to a 50–80° aqueous or alcoholic solution containing either one or two equivalents of either the (D) or (L) enantiomer of a natural amino acid. Upon slowly cooling, crystals of the desired complex form and can be isolated by filtration.

Compounds of formula I can be prepared as shown in Scheme 1 by treatment of compounds of formula II

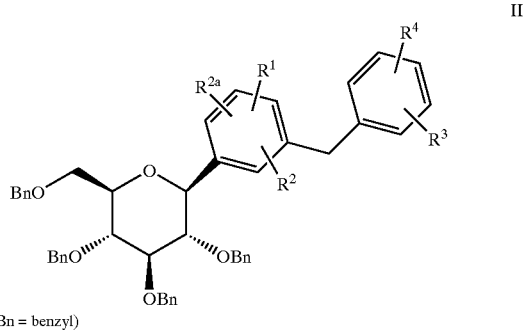

(where Bn = benzyl)

with $H_2$ in the presence of a catalyst such as 1) Pd/C employing a solvent such as MeOH or EtOH or 2) preferably $Pd(OH)_2$ using a solvent such as EtOAc. Alternatively, compounds of formula I can be prepared by treatment of compounds of formula II with a Lewis acid such $BBr_3$, $BCl_3$, or $BCl_3 \cdot Me_2S$ in a solvent such as $CH_2Cl_2$ at −78°. Compounds of formula I can also be prepared by treatment of compounds of formula II in a solvent such as EtSH containing $BF_3 \cdot Et_2O$, at 20°.

Compounds of formula II can be prepared by treatment of compounds of formula III with silanes such as $Et_3SiH$ or preferably $(iPr)_3SiH$ in a solvent such as MeCN or mixtures of $MeCN/CH_2Cl_2$ containing a Lewis acid such as $BF_3 \cdot Et_2O$ at −30°.

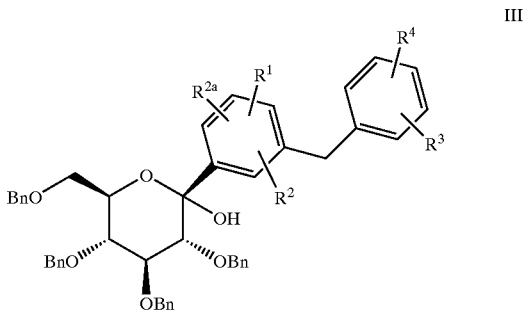

Compounds of formula III can be prepared by coupling of a compound of formula IV

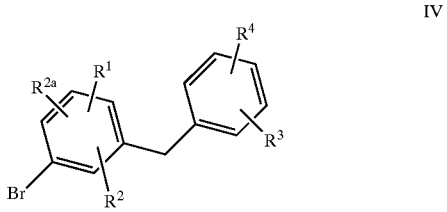

with compound V

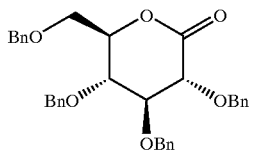

V

Compounds of formula IV are activated for coupling by treatment with n-BuLi or t-BuLi at −78° in a solvent such as THF prior to addition of lactone V. Preparation of lactone V is described in. R. Benhaddou, S Czernecki, et al., *Carbohydr. Res.*, 260 (1994), 243–250.

Scheme 1

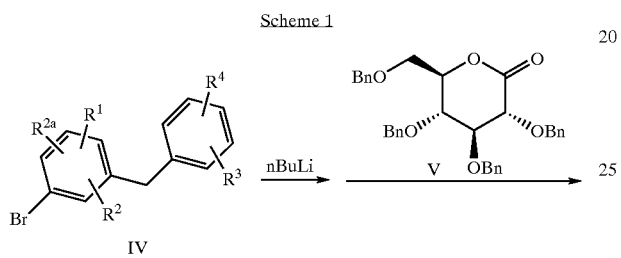

Compounds of formula IV can be prepared as shown in Scheme 2 by treatment of compounds of formula VI

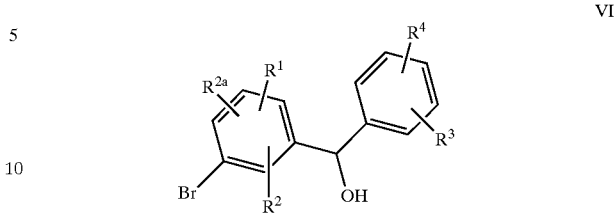

VI with silanes such as $Et_3SiH$ in a solvent such as MeCN or $CH_2Cl_2$ containing a Lewis acid such as $BF_3 \cdot Et_2O$ or TFA at −30° to +60°.

Compounds of formula VI can be prepared by coupling commercially available bromobenzaldehydes of formula VII

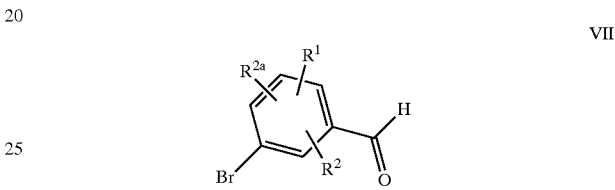

VII with either the lithium or magnesium organometalic derivative of compounds of formula VIII

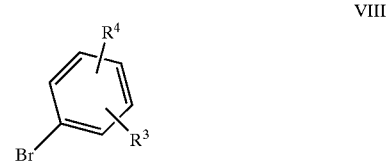

VIII in a solvent such as $Et_2O$ or THF using conditions familiar to those skilled in the art.

Compounds of formula VIII are either commercially available or readily prepared by standard methods known to those skilled in the art.

Scheme 2

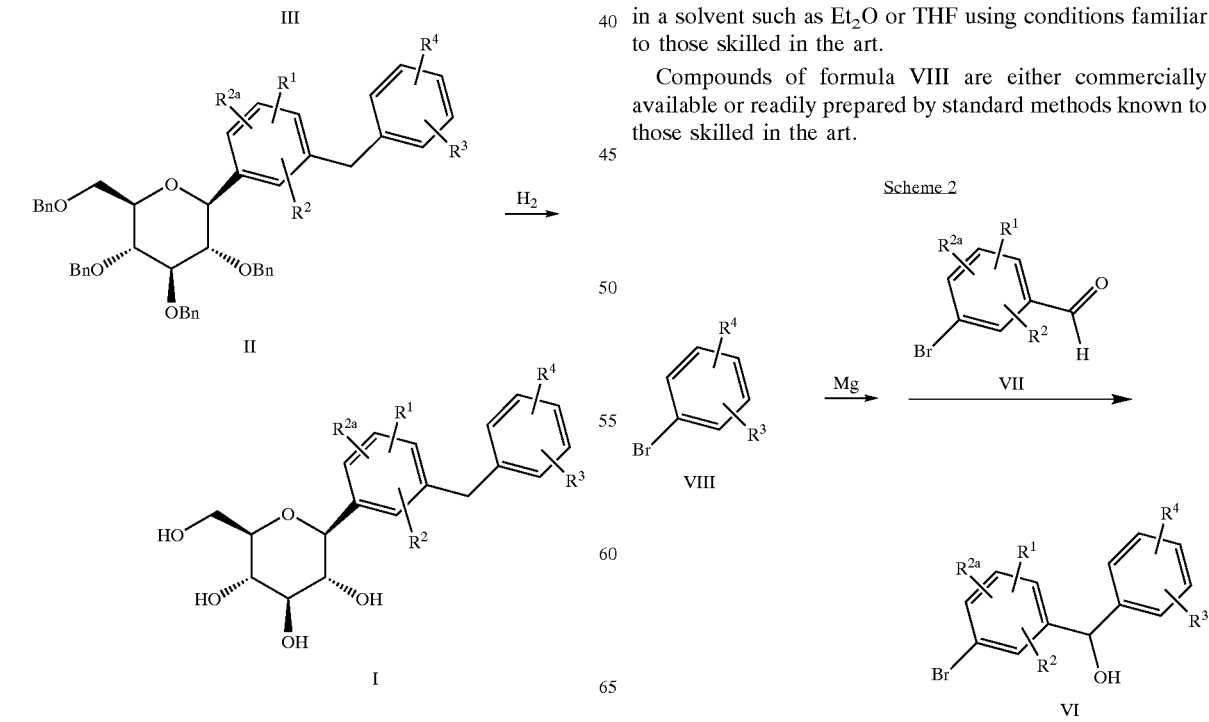

VI $\xrightarrow{\text{Et}_3\text{SiH}}$

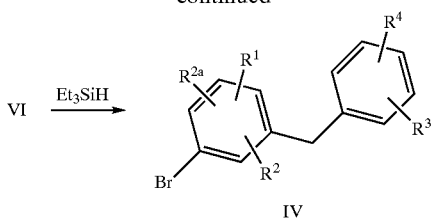

IV

Compounds of formula I where $R^4$ is $CH(OR^{5h})R^{6d}$ can be prepared by treatment of compounds of formula I where $R^4$ is $COR^{6b}$ sequentially with 1) an acetylating agent such as $Ac_2O$ in a solvent such as pyridine alone or $CH_2Cl_2$ containing 1.5 equivalents of a base such as $Et_3N$, 2) a reducing agent such as $NaBH_4$ in a solvent such as EtOH, 3) an alkylating agent such as $R^{5h}Br$ or $R^{5h}I$ in the presence of a base such as NAH in a solvent such as DMF, and 4) alkaline ester hydrolysis conditions such as LiOH in a 2:3:1 mixture of $THF/MeOH/H_2O$.

Compounds of formula I where $R^4$ is $CH(OH)R^{6c}$ can be prepared by treatment of compounds of formula I where $R^4$ is $COR^{6b}$ with a reducing agent such as $NaBH_4$ in a solvent such as EtOH.

Compounds of formula I where $R^4$ is $COR^{6b}$ can be prepared by treatment of compounds of formula II where $R^4$ is $COR^{6b}$ with a Lewis acid such as $BCl_3$ or $BBr_3$ at $-78°$ in a solvent such as $CH_2Cl_2$.

Compounds of formula II where A is $CH_2$ and $R^4$ is $-COR^{6b}$ can be prepared as shown in Scheme 3 by coupling commercially available or readily accessible compounds of formula IX

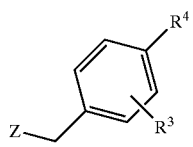

IX where Z is Br or Cl with compounds of formula X

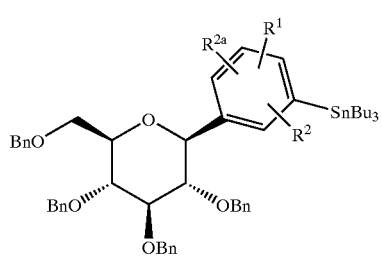

X by heating the two components in a solvent such as PhMe in the presence of a catalyst such as $Pd(PPh_3)_4$.

Compounds of formula X can be prepared from compounds of formula XI

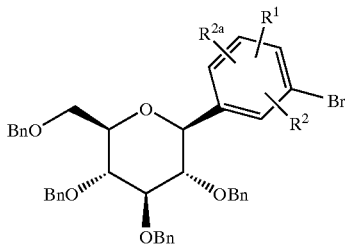

XI by treatment with $(Bu_3Sn)_2$ and a catalyst such as $Pd(Ph_3P)_4$ in a solvent such as toluene.

Compounds of formula XI can be prepared from compounds of formula XII

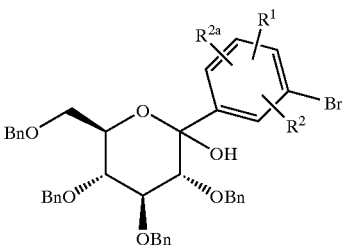

XII by treatment with silanes such as $iPr_3SiH$ or $Et_3SiH$ in a solvent such as MeCN containing a Lewis acid such as $BF_3 \cdot Et_2O$ at $-30°$.

Compounds of formula XII can be prepared by coupling compound V with the organolithium obtained upon treatment of compounds of formula XIII

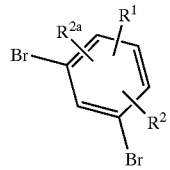

XIII with n-BuLi or t-BuLi at $-78°$ in THF.

Scheme 3

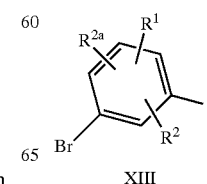

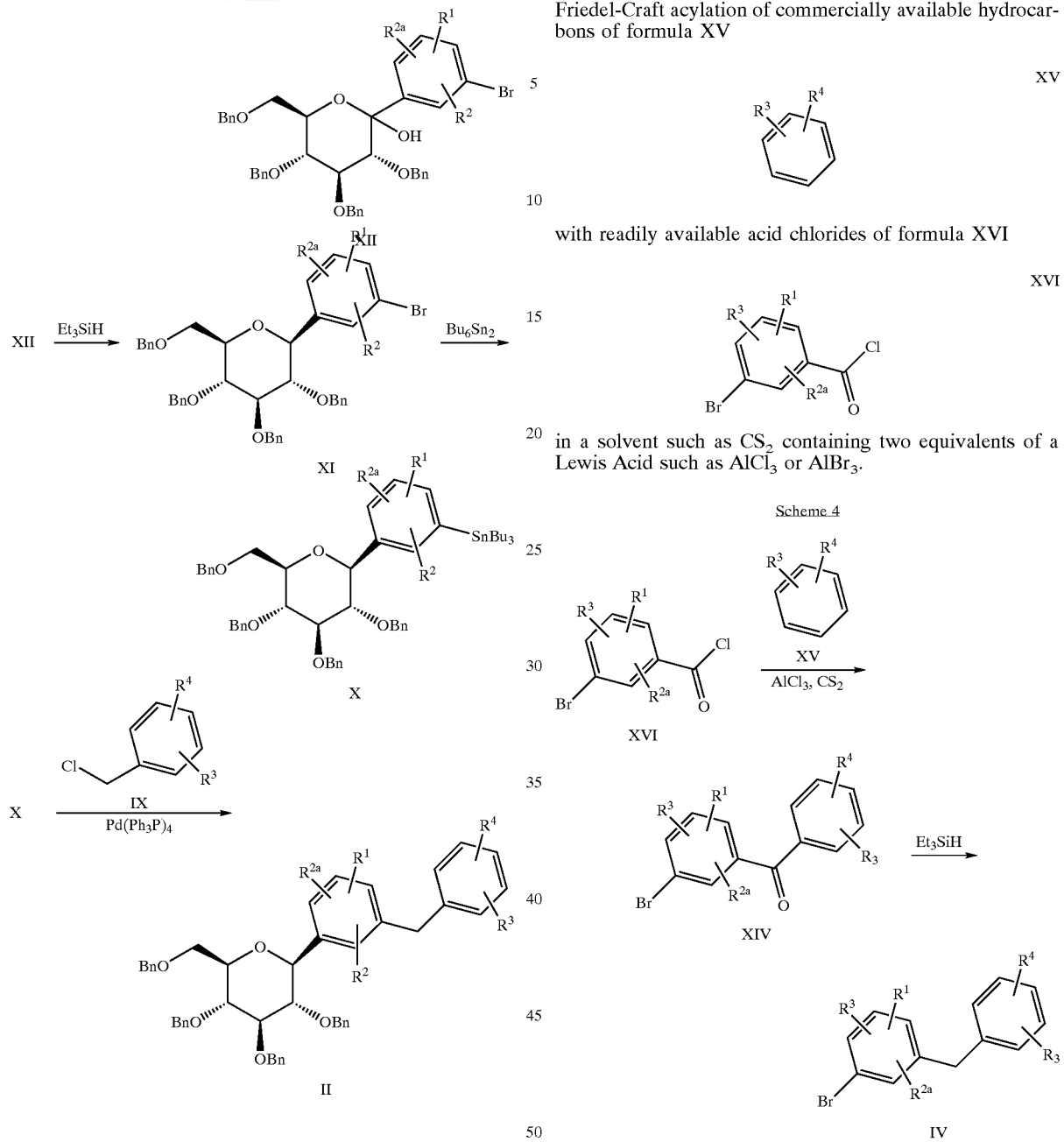

Compounds of formula XIV can be readily prepared by Friedel-Craft acylation of commercially available hydrocarbons of formula XV

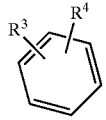

with readily available acid chlorides of formula XVI in a solvent such as $CS_2$ containing two equivalents of a Lewis Acid such as $AlCl_3$ or $AlBr_3$.

An alternative synthesis (Scheme 4) of compounds of formula IV entails reduction of compounds of formula XIV with a reducing agent such as $Et_3SiH$ in a solvent such as MeCN or $CH_2Cl_2$ or mixtures thereof containing a catalyst such as $BF_3Et_2O$.

Compounds of formula II, where $R^2$=OH, can be prepared as shown in Scheme 5 upon sequential treatment of compounds of formula XXI

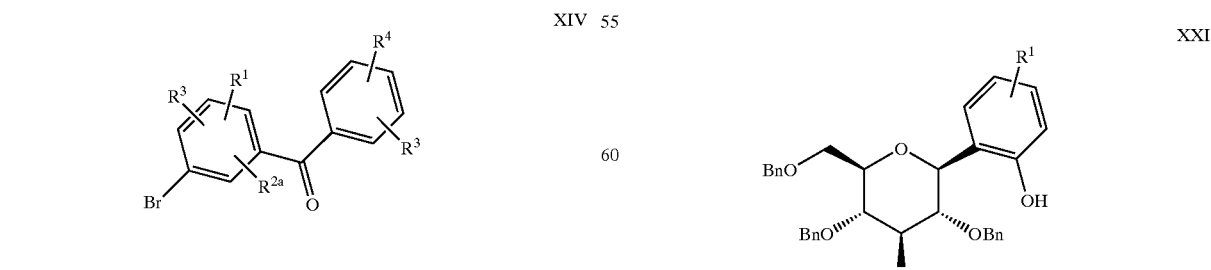

with a base such as NaH followed by heating with compounds of formula IX in a solvent such as PhMe.

Compounds of formula XXI can be prepared from compounds of formula XXII

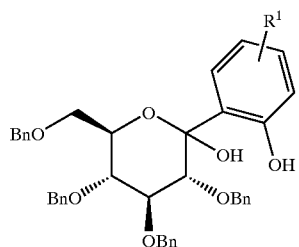
XXII by treatment with silanes such as Et₃SiH or i-Pr₃SiH in a solvent such as MeCN containing a Lewis acid such as BF₃·Et₂O at −30°.

Compounds of formula XXII can be prepared by coupling the compound of formula V with activated metallated derivatives of compounds of formula XXIII

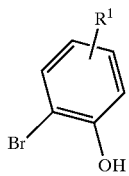

which are prepared by sequential treatment of XXIII with a base such as NaH, KH, or KOtBu followed by an alkyllithium such as nBuLi or tBuLi in a solvent such as dry THF.

Scheme 5

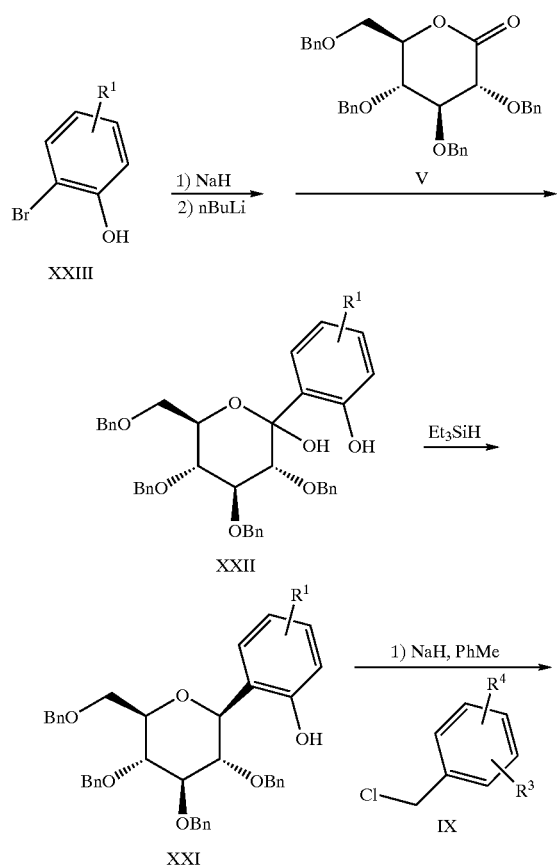

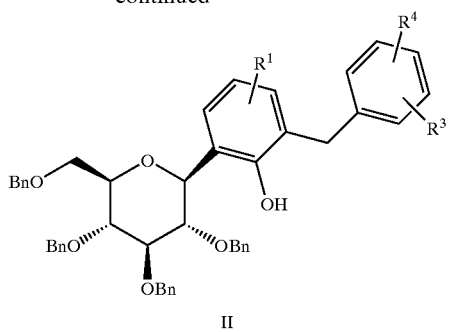
II

Listed below are definitions of various terms used in the description of the instant invention. These definitions apply to the terms as they are used throughout the specification (unless they are otherwise limited in specific instances) either individually or as part of a larger group.

The following abbreviations are employed herein:

Me=methyl
Et=ethyl
THF=tetrahydrofuran
Et₂O=diethyl ether
EtOAc=ethyl acetate
DMF=dimethyl formamide
MeOH=methanol
EtOH=ethanol
i-PrOH=isopropanol
HOAc or AcOH=acetic acid
TFA=trifluoroacetic acid
Et₃N=triethylamine
Ar=argon
N₂=nitrogen
min=minute(s)
h or hr=hour(s)
L=liter
mL=milliliter
μL=microliter
g=gram(s)
mg=milligram(s)
mol=moles
mmol=millimole(s)
meq=milliequivalent
RT=room temperature
sat or sat'd=saturated
aq.=aqueous
TLC=thin layer chromatography
HPLC=high performance liquid chromatography
LC/MS=high performance liquid chromatography/mass spectrometry
MS or Mass Spec=mass spectrometry
NMR=nuclear magnetic resonance
mp=melting point Unless otherwise indicated, the term "lower alkyl" as employed herein alone or as part of another group includes both straight and branched chain hydrocarbons containing 1 to 8 carbons, and the terms "alkyl" and "alk" as employed herein alone or as part of another group includes both straight and branched chain hydrocarbons containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1 to 4 substituents such as halo, for example F, Br, Cl or I or $CF_3$, alkyl, alkoxy, aryl, aryloxy, aryl(aryl) or diaryl, arylalkyl, arylalkyloxy, alkenyl, alkynyl, cycloalkyl, cycloalkenyl, cycloalkylalkyl, cycloalkylalkyloxy, optionally substituted amino, hydroxy, hydroxyalkyl, acyl, alkanoyl, heteroaryl, heteroaryloxy, cycloheteroalkyl, arylheteroaryl, arylalkoxycarbonyl, heteroarylalkyl, heteroarylalkoxy, aryloxyalkyl, aryloxyaryl, alkylamido, alkanoylamino, arylcarbonylamino, nitro, cyano, thiol, haloalkyl, trihaloalkyl and/or alkylthio.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

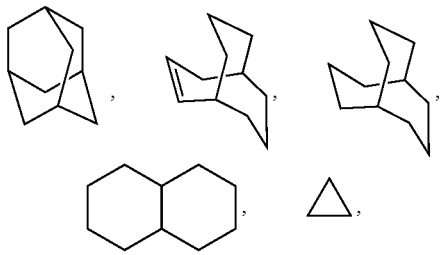

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol and/or alkylthio and/or any of the alkyl substituents.

The term "cycloalkenyl" as employed herein alone or as part of another group refers to cyclic hydrocarbons containing 3 to 12 carbons, preferably 5 to 10 carbons and 1 or 2 double bonds. Exemplary cycloalkenyl groups include cyclopentenyl, cyclohexenyl, cycloheptenyl, cyclooctenyl, cyclohexadienyl, and cycloheptadienyl, which may be optionally substituted as defined for cycloalkyl.

The term "alkanoyl" as used herein alone or as part of another group refers to alkyl linked to a carbonyl group.

Unless otherwise indicated, the term "lower alkenyl" as used herein by itself or as part of another group refers to straight or branched chain radicals of 2 to 8 carbons, and the term "alkenyl" as used herein by itself or as part of another group refers to straight or branched chain redicals of 2 to 20 carbons, preferably 2 to 12 carbons, and more preferably 2 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonylamino, nitro, cyano, thiol, alkylthio and/or any of the alkyl substituents set out herein.

Unless otherwise indicated, the term "lower alkynyl" as used herein by itself or as part of another group refers to straight or branched chain radicals of 2 to 8 carbons, and the term "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the alkyl substituents set out herein.

The terms "arylakyl", "arylalkenyl" and "arylalkynyl" as used alone or as part of another group refer to alkyl, alkenyl and alkynyl groups as described above having an aryl substituent.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

Suitable alkylene, alkenylene or alkynylene groups $(CH_2)_m$ or $(CH_2)_p$ (where p is 1 to 8, preferably 1 to 5, and m is 1 to 5, preferably 1 to 3, which includes alkylene, alkenylene or alkynylene groups) as defined herein, may optionally include 1, 2, or 3 substituents which include alkyl, alkenyl, halogen, cyano, hydroxy, alkoxy, amino, thioalkyl, keto, $C_3$–$C_6$ cycloalkyl, alkylcarbonylamino or alkylcarbonyloxy.

Examples of $(CH_2)_m$ or $(CH_2)_p$, alkylene, alkenylene and alkynylene include

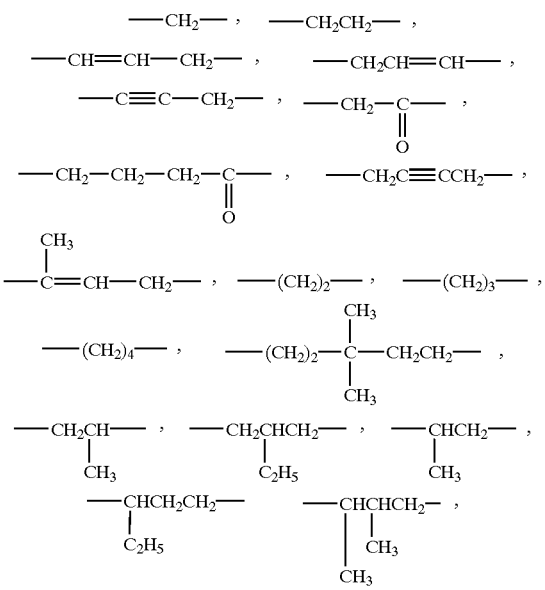

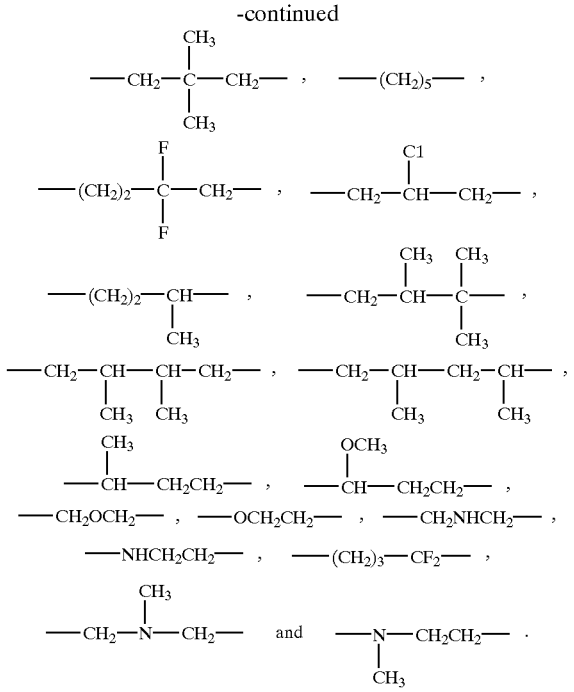

The term "halogen" or "halo" as used herein alone or as part of another group refers to chlorine, bromine, fluorine, and iodine, with chlorine or fluorine being preferred.

The term "metal ion" refers to alkali metal ions such as sodium, potassium or lithium and alkaline earth metal ions such as magnesium and calcium, as well as zinc and aluminum.

Unless otherwise indicated, the term "aryl" or "Aryl" as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings for example

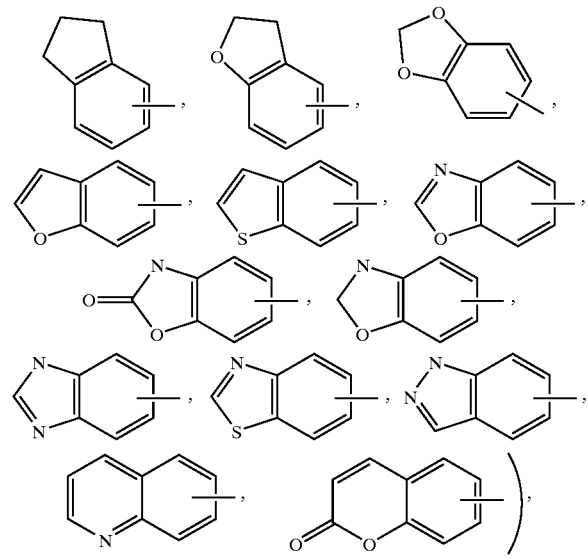

and may be optionally substituted through available carbon atoms with 1, 2, or 3 groups selected from hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino and arylsulfonaminocarbonyl and/or any of the alkyl substituents set out herein.

Unless otherwise indicated, the term "lower alkoxy", "alkoxy", "aryloxy" or "aralkoxy" as employed herein alone or as part of another group includes any of the above alkyl, aralkyl or aryl groups linked to an oxygen atom.

Unless otherwise indicated, the term "substituted amino" as employed herein alone or as part of another group refers to amino substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl and thioalkyl. These substituents may be further substituted with a carboxylic acid and/or any of the alkyl substituents as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, alkoxy, alkylthio, halo, trifluoromethyl or hydroxy.

Unless otherwise indicated, the term "lower alkylthio", alkylthio", "arylthio" or "aralkylthio" as employed herein alone or as part of another group includes any of the above alkyl, aralkyl or aryl groups linked to a sulfur atom.

Unless otherwise indicated, the term "lower alkylamino", "alkylamino", "arylamino", or "arylalkylamino" as employed herein alone or as part of another group includes any of the above alkyl, aryl or arylalkyl groups linked to a nitrogen atom.

Unless otherwise indicated, the term "acyl" as employed herein by itself or as part of another group, as defined herein, refers to an organic radical linked to a carbonyl

group; examples of acyl groups include any of the alkyl substituents attached to a carbonyl, such as alkanoyl, alkenoyl, aroyl, aralkanoyl, heteroaroyl, cycloalkanoyl, cycloheteroalkanoyl and the like.

Unless otherwise indicated, the term "cycloheteroalkyl" as used herein alone or as part of another group refers to a 5-, 6- or 7-membered saturated or partially unsaturated ring which includes 1 to 2 hetero atoms such as nitrogen, oxygen and/or sulfur, linked through a carbon atom or a heteroatom, where possible, optionally via the linker $(CH_2)_p$ (where p is 1, 2 or 3), such as

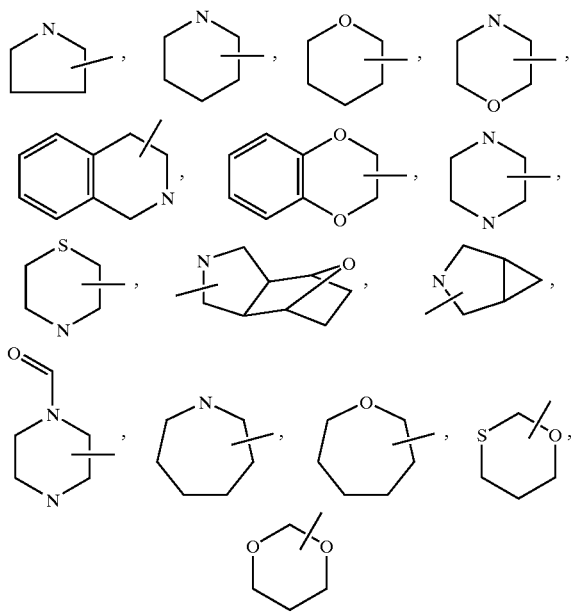

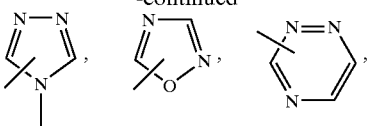

and the like. The above groups may include 1 to 4 substituents such as alkyl, halo, oxo and/or any of the alkyl substituents set out herein. In addition, any of the cycloheteroalkyl rings can be fused to a cycloalkyl, aryl, heteroaryl or cycloheteroalkyl ring.

Unless otherwise indicated, the term "heteroaryl" as used herein alone or as part of another group refers to a 5- or 6-membered aromatic ring which includes 1, 2, 3 or 4 hetero atoms such as nitrogen, oxygen or sulfur, and such rings fused to an aryl, cycloalkyl, heteroaryl or cycloheteroalkyl ring (e.g., benzothiophenyl or indolyl), and includes possible N-oxides. The heteroaryl group may optionally include 1 to 4 substituents such as any of the the alkyl substituents set out above. Examples of heteroaryl groups include the following:

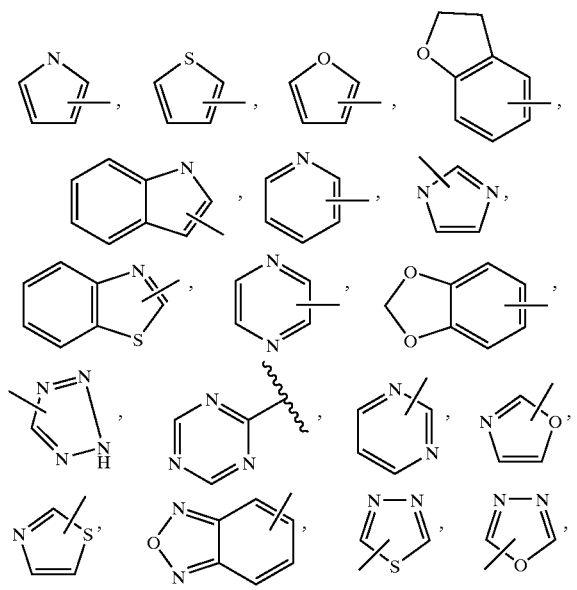

and the like.

The term "cycloheteroalkylalkyl" as used herein alone or as part of another group refers to cycloheteroalkyl groups as defined above linked through a C atom or heteroatom to a $(CH_2)_p$ chain.

The term "heteroarylalkyl" or "heteroarylalkenyl" as used herein alone or as part of another group refers to a heteroaryl group as defined above linked through a C atom or heteroatom to a $—(CH_2)_p—$ chain, alkylene or alkenylene as defined above.

The term "five, six or seven membered carbocycle or heterocycle" as employed herein refers to cycloalkyl or cycloalkenyl groups as defined above or heteroaryl groups or cycloheteroaryl groups as defined above, such as thiadiazaole, tetrazole, imidazole, or oxazole.

The term "polyhaloalkyl" as used herein refers to an "alkyl" group as defined above which includes from 2 to 9, preferably from 2 to 5, halo substituents, such as F or Cl, preferably F, such as $CF_3CH_2$, $CF_3$ or $CF_3CF_2CH_2$.

The term "polyhaloalkyloxy" as used herein refers to an "alkoxy" or "alkyloxy" group as defined above which includes from 2 to 9, preferably from 2 to 5, halo substituents, such as F or Cl, preferably F, such as $CF_3CH_2O$, $CF_3O$ or $CF_3CF_2CH_2O$.

All stereoisomers of the compounds of the instant invention are contemplated, either in admixture or in pure or substantially pure form. The compounds of the present invention can have asymmetric centers at any of the carbon atoms including any one of the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic or fractional crystallization.

Where desired, complexes of either the (D) or (L) enantiomer of natural amino acids with compounds of formula I may be used in combination with one or more other types of antidiabetic agents and/or one or more other types of therapeutic agents which may be administered orally in the same dosage form, in a separate oral dosage form or by injection.

The other type of antidiabetic agent which may be optionally employed in combination with complexes of either the (D) or (L) enantiomer of natural amino acids with a SGLT2 inhibitor of formula I may be 1,2,3 or more antidiabetic agents or antihyperglycemic agents including insulin secretagogues or insulin sensitizers, or other antidiabetic agents preferably having a mechanism of action different from SGLT2 inhibition and may include biguamides, sulfonyl ureas, glucosidase inhibitors, PPAR γ agonists such as thiazolidinediones, aP2 inhibitors, PPAR α/γ dual agonists, dipeptidyl peptidase IV (DP4) inhibitors, and/or meglitinides, as well as insulin, glucagon-like peptide-1 (GLP-1), PTP1B inhibitors, glycogen phosphorylase inhibitors and/or glucos-6-phosphatase inhibitors.

The other types of therapeutic agents which may be optionally employed in combination with complexes of either the (D) or (L) enantiomer of natural amino acids with SGLT2 inhibitors of formula I include anti-obesity agents, antihypertensive agents, antiplatelet agents, antiatherosclerotic agents and/or lipid lowering agents.

The complexes of either the (D) or (L) enantiomer of natural amino acids with SGLT2 inhibitors of formula I may also be optionally employed in combination with agents for treating complications of diabetes. These agents include PKC inhibitors and/or AGE inhibitors.

It is believed that the use of complexes of either the (D) or (L) enantiomer of natural amino acids with compounds of formula I in combination with 1, 2, 3 or more other antidiabetic agents produces antihyperglycemic results greater than that possible from each of these medicaments alone and greater than the combined additive anti-hyperglycemic effects produced by these medicaments.

The other antidiabetic agent may be an oral antihyperglycemic agent preferably a biguanide such as metformin or phenformin or salts thereof, preferably metformin HCl.

Where the other antidiabetic agent is a biguanide, the compounds of formula I will be employed in a weight ratio to biguanide within the range from about 0.01:1 to about 100:1, preferably from about 0.1:1 to about 5:1.

The other antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the β-cells, with glyburide and glipizide being preferred, which may be administered in the same or in separate oral dosage forms.

The complexes of either the (D) or (L) enantiomer of natural amino acids with compounds of formula I will be employed in a weight ratio to the sulfonyl urea in the range from about 0.01:1 to about 100:1, preferably from about 0.2:1 to about 10:1.

The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The complexes of either the (D) or (L) enantiomer of natural amino acids with compounds of formula I will be employed in a weight ratio to the glucosidase inhibitor within the range from about 0.01:1 to about 100:1, preferably from about 0.5:1 to about 50:1.

The complexes of either the (D) or (L) enantiomer of natural amino acids with compounds of formula I may be employed in combination with a PPAR γ agonist such as a thiazolidinedione oral anti-diabetic agent or other insulin sensitizers (which has an insulin sensitivity effect in NIDDM patients) such as troglitazone (Warner-Lambert's Rezulin®, disclosed in U.S. Pat. No. 4,572,912), rosiglitazone (SKB), pioglitazone (Takeda), Mitsubishi's MCC-555 (disclosed in U.S. Pat. No. 5,594,016), Glaxo-Welcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), NN-2344 (Dr. Reddy/NN), or YM-440 (Yamanouchi), preferably rosiglitazone and pioglitazone.

The complexes of either the (D) or (L) enantiomer of natural amino acids with compounds of formula I will be employed in a weight ratio to the thiazolidinedione in an amount within the range from about 0.01:1 to about 100:1, preferably from about 0.2:1 to about 10:1.

The sulfonyl urea and thiazolidinedione in amounts of less than about 150 mg oral antidiabetic agent may be incorporated in a single tablet with the complexes of either the (D) or (L) enantiomer of natural amino acids with compounds of formula I.

The complexes of either the (D) or (L) enantiomer of natural amino acids with compounds of formula I may also be employed in combination with an antihyperglycemic agent such as insulin or with glucagon-like peptide-1 (GLP-1) such as GLP-1(1–36) amide, GLP-1(7–36) amide, GLP-1(7–37) (as disclosed in U.S. Pat. No. 5,614,492 to Habener, the disclosure of which is incorporated herein by reference), as well as AC2993 (Amylen) and LY-315902 (Lilly), which may be administered via injection, intranasal, or by transdermal or buccal devices.

Where present, metformin, the sulfonyl ureas, such as glyburide, glimepiride, glipyride, glipizide, chlorpropamide and gliclazide and the glucosidase inhibitors acarbose or miglitol or insulin (injectable, pulmonary, buccal, or oral) may be employed in formulations as described above and in amounts and dosing as indicated in the Physician's Desk Reference (PDR).

Where present, metformin or salt thereof may be employed in amounts within the range from about 500 to about 2000 mg per day which may be administered in single or divided doses one to four times daily.

Where present, the thiazolidinedione anti-diabetic agent may be employed in amounts within the range from about 0.01 to about 2000 mg/day which may be administered in single or divided doses one to four times per day.

Where present insulin may be employed in formulations, amounts and dosing as indicated by the Physician's Desk Reference.

Where present GLP-1 peptides may be administered in oral buccal formulations, by nasal administration or parenterally as described in U.S. Pat. No. 5,346,701 (TheraTech), U.S. Pat. Nos. 5,614,492 and 5,631,224 which are incorporated herein by reference.

The other antidiabetic agent may also be a PPAR a/y dual agonist such as AR-HO39242 (Astra/Zeneca), GW-409544 (Glaxo-Wellcome), KRP297 (Kyorin Merck) as well as those disclosed by Murakami et al, "A Novel Insulin Sensitizer Acts As a Coligand for Peroxisome Proliferation—Activated Receptor Alpha (PPAR alpha) and PPAR gamma. Effect on PPAR alpha Activation on Abnormal Lipid Metabolism in Liver of Zucker Fatty Rats", Diabetes 47, 1841–1847 (1998), and in U.S. provisional application No. 60/155,400, filed Sep. 22, 1999, the disclosure of which is incorporated herein by reference, employing dosages as set out therein, which compounds designated as preferred are preferred for use herein.

The other antidiabetic agent may be an aP2 inhibitor such as disclosed in U.S. application Ser. No. 09/391,053, filed Sep. 7, 1999, and in U.S. provisional application No. 60/127, 745, filed Apr. 5, 1999 employing dosages as set out herein. Preferred are the compounds designated as preferred in the above application.

The other antidiabetic agent may be a DP4 inhibitor such as disclosed in WO99/38501, WO99/46272, WO99/67279 (PROBIODRUG), WO99/67278 (PROBIODRUG), WO99/61431 (PROBIODRUG), NVP-DPP728A (1-[[[2-[(5-cyanopyridin-2-yl)amino]ethyl]amino]acetyl]-2-cyano-(S)-pyrrolidine) (Novartis) (preferred) as disclosed by Hughes et al, Biochemistry, 38(36), 11597–11603, 1999, TSL-225 (tryptophyl-1,2,3,4-tetrahydroisoquinoline-3-carboxylic acid (disclosed by Yamada et al, Bioorg. & Med. Chem. Lett. 8 (1998) 1537–1540, 2-cyanopyrrolidides and 4-cyanopyrrolidides as disclosed by Ashworth et al, Bioorg. & Med. Chem. Lett., Vol. 6, No. 22, pp 1163–1166 and 2745–2748 (1996) employing dosages as set out in the above references.

The meglitinide which may optionally be employed in combination with the complexes of either the (D) or (L)

enantiomer of natural amino acids with compounds of formula I of the invention may be repaglinide, nateglinide (Novartis) or KAD1229 (PF/Kissei), with repaglinide being preferred.

The complexes of either the (D) or (L) enantiomer of natural amino acids with compounds of formula I will be employed in a weight ratio to the meglitinide, PPAR γ agonist, PPAR α/γ dual agonist, aP2 inhibitor or DP4 inhibitor within the range from about 0.01:1 to about 100:1, preferably from about 0.2:1 to about 10:1.

The hypolipidemic agent or lipid-lowering agent which may be optionally employed in combination with complexes of either the (D) or (L) enantiomer of natural amino acids with compounds of formula I of the invention may include 1,2,3 or more MTP inhibitors, HMG CoA reductase inhibitors, squalene synthetase inhibitors, fibric acid derivatives, ACAT inhibitors, lipoxygenase inhibitors, cholesterol absorption inhibitors, ileal $Na^+$/bile acid cotransporter inhibitors, upregulators of LDL receptor activity, bile acid sequestrants, and/or nicotinic acid and derivatives thereof.

MTP inhibitors employed herein include MTP inhibitors disclosed in U.S. Pat. No. 5,595,872, U.S. Pat. No. 5,739,135, U.S. Pat. No. 5,712,279, U.S. Pat. No. 5,760,246, U.S. Pat. No. 5,827,875, U.S. Pat. No. 5,885,983 and U.S. application Ser. No. 09/175,180 filed Oct. 20, 1998, now U.S. Pat. No. 5,962,440. Preferred are each of the preferred MTP inhibitors disclosed in each of the above patents and applications. All of the above U.S. Patents and applications are incorporated herein by reference.

The hypolipidemic agent may be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. The hypolipidemic agent may also be the compounds disclosed in U.S. provisional application nos. 60/211,594 and 60/211,595. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, atavastatin (Nissan/Sankyo's nisvastatin (NK-104)) disclosed in U.S. Pat. No. 5,011,930, Shionogi-Astra/Zeneca visastatin (ZD-4522) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0,142,146 A2, and quinoline and pyridine derivatives disclosed in U.S. Pat. Nos. 5,506,219 and 5,691,322.

In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller et al, J. Med. Chem., 1988, Vol. 31, No. 10, pp 1869–1871, including isoprenoid (phosphinyl-methyl) phosphonates as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., Current Pharmaceutical Design, 2, 1–40 (1996).

In addition, other squalene synthetase inhibitors suitable for use herein include the terpenoid pyrophosphates disclosed by P. Ortiz de Montellano et al, J. Med. Chem., 1977, 20, 243–249, the farnesyl diphosphate analog A and presqualene pyrophosphate (PSQ-PP) analogs as disclosed by Corey and Volante, J. Am. Chem. Soc., 1976, 98, 1291–1293, phosphinylphosphonates reported by McClard, R. W. et al, J.A.C.S., 1987, 109, 5544 and cyclopropanes reported by Capson, T. L., PhD dissertation, June, 1987, Dept. Med. Chem. U of Utah, Abstract, Table of Contents, pp 16, 17, 40–43, 48–51, Summary.

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (Secholex®, Policexide®), as well as lipostabil (Rhone-Poulenc), Eisai E-5050 (an N-substituted ethanolamine derivative), imanixil (HOE-402), tetrahydrolipstatin (THL), istigmastanylphosphorylcholine (SPC, Roche), aminocyclodextrin (Tanabe Seiyoku), Ajinomoto AJ-814 (azulene derivative), melinamide (Sumitomo), Sandoz 58–035, American Cyanamid CL-277,082 and CL-283,546 (disubstituted urea derivatives), nicotinic acid, acipimox, acifran, neomycin, p-aminosalicylic acid, aspirin, poly (diallylmethylamine) derivatives such as disclosed in U.S. Pat. No. 4,759,923, quaternary amine poly (diallyldimethylammonium chloride) and ionenes such as disclosed in U.S. Pat. No. 4,027,009, and other known serum cholesterol lowering agents.

The other hypolipidemic agent may be an ACAT inhibitor such as disclosed in, Drugs of the Future 24, 9–15 (1999), (Avasimibe); "The ACAT inhibitor, Cl-1011 is effective in the prevention and regression of aortic fatty streak area in hamsters", Nicolosi et al, Atherosclerosis (Shannon, Irel). (1998), 137(1), 77–85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16–30; "RP 73163: a bioavailable alkylsulfinyl-diphenylimidazole ACAT inhibitor", Smith, C., et al, Bioorg. Med. Chem. Lett. (1996), 6(1), 47–50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173–98, Publisher: CRC, Boca Raton, Fla.; "ACAT inhibitors: potential anti-atherosclerotic agents", Sliskovic et al, Curr. Med. Chem. (1994), 1(3), 204–25; "Inhibitors of acyl-CoA:cholesterol O-acyl transferase (ACAT) as hypocholesterolemic agents. 6. The first water-soluble ACAT inhibitor with lipid-regulating activity.

Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. (1995), 8(6), 359–62, or TS-962 (Taisho Pharmaceutical Co. Ltd).

The hypolipidemic agent may be an upregulator of LD2 receptor activity such as MD-700 (Taisho Pharmaceutical Co. Ltd) and LY295427 (Eli Lilly).

The hypolipidemic agent may be a cholesterol absorption inhibitor preferably Schering-Plough's SCH48461 as well as those disclosed in Atherosclerosis 115, 45–63 (1995) and J. Med. Chem. 41, 973 (1998).

The hypolipidemic agent may be an ileal $Na^+$/bile acid cotransporter inhibitor such as disclosed in Drugs of the Future, 24, 425–430 (1999).

Preferred hypolipidemic agents are pravastatin, lovastatin, simvastatin, atorvastatin, fluvastatin, cerivastatin, atavastatin and rosuvastatin.

The above-mentioned U.S. patents are incorporated herein by reference. The amounts and dosages employed will be as indicated in the Physician's Desk Reference and/or in the patents set out above.

The complexes of either the (D) or (L) enantiomer of natural amino acids with compounds of formula I of the invention will be employed in a weight ratio to the hypolipidemic agent (where present), within the range from about 500:1 to about 1:500, preferably from about 100:1 to about 1:100.

The dose administered must be carefully adjusted according to age, weight and condition of the patient, as well as the route of administration, dosage form and regimen and the desired result.

The dosages and formulations for the hypolipidemic agent will be as disclosed in the various patents and applications discussed above.

The dosages and formulations for the other hypolipidemic agent to be employed, where applicable, will be as set out in the latest edition of the Physicians' Desk Reference.

For oral administration, a satisfactory result may be obtained employing the MTP inhibitor in an amount within the range of from about 0.01 mg/kg to about 500 mg and preferably from about 0.1 mg to about 100 mg, one to four times daily.

A preferred oral dosage form, such as tablets or capsules, will contain the MTP inhibitor in an amount of from about 1 to about 500 mg, preferably from about 2 to about 400 mg, and more preferably from about 5 to about 250 mg, one to four times daily.

For oral administration, a satisfactory result may be obtained employing an HMG CoA reductase inhibitor, for example, pravastatin, lovastatin, simvastatin, atorvastatin, fluvastatin or cerivastatin in dosages employed as indicated in the Physician's Desk Reference, such as in an amount within the range of from about 1 to 2000 mg, and preferably from about 4 to about 200 mg.

The squalene synthetase inhibitor may be employed in dosages in an amount within the range of from about 10 mg to about 2000 mg and preferably from about 25 mg to about 200 mg.

A preferred oral dosage form, such as tablets or capsules, will contain the HMG CoA reductase inhibitor in an amount from about 0.1 to about 100 mg, preferably from about 5 to about 80 mg, and more preferably from about 10 to about 40 mg.

A preferred oral dosage form, such as tablets or capsules will contain the squalene synthetase inhibitor in an amount of from about 10 to about 500 mg, preferably from about 25 to about 200 mg.

The other hypolipidemic agent may also be a lipoxygenase inhibitor including a 15-lipoxygenase (15-LO) inhibitor such as benzimidazole derivatives as disclosed in WO 97/12615, 15-LO inhibitors as disclosed in WO 97/12613, isothiazolones as disclosed in WO 96/38144, and 15-LO inhibitors as disclosed by Sendobry et al "Attenuation of diet-induced atherosclerosis in rabbits with a highly selective 15-lipoxygenase inhibitor lacking significant antioxidant properties, Brit. J. Pharmacology (1997) 120, 1199–1206, and Cornicelli et al, "15-Lipoxygenase and its Inhibition: A Novel Therapeutic Target for Vascular Disease", Current Pharmaceutical Design, 1999, 5, 11–20.

The complexes of either the (D) or (L) enantiomer of natural amino acids with compounds of formula I and the hypolipidemic agent may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

The preferred hypolipidemic agents are pravastatin, simvastatin, lovastatin, atorvastatin, fluvastatin, cerivastatin, atavastatin and rosuvastatin.

When the other type of therapeutic agent which may be optionally employed with the complexes of either the (D) or (L) enantiomer of natural amino acids with compounds of formula I is 1, 2, 3 or more of an anti-obesity agent, it may include a beta 3 adrenergic agonist, a lipase inhibitor, a serotonin (and dopamine) reuptake inhibitor, a thyroid receptor beta drug, an anorectic agent, an NPY antagonist, a Leptin analog and/or an MC4 agonist.

The beta 3 adrenergic agonist which may be optionally employed in combination with complexes of either the (D) or (L) enantiomer of natural amino acids with compounds of formula I may be AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, with AJ9677, L750, 355 and CP331648 being preferred.

The lipase inhibitor which may be optionally employed in combination with complexes of either the (D) or (L) enantiomer of natural amino acids with compounds of formula I may be orlistat or ATL-962 (Alizyme), with orlistat being preferred.

The serotonin (and dopamine) reuptake inhibitor which may be optionally employed in combination with complexes of either the (D) or (L) enantiomer of natural amino acids with compounds of formula I may be sibutramine, topiramate (Johnson & Johnson) or axokine (Regeneron), with sibutramine and topiramate being preferred.

The thyroid receptor beta compound which may be optionally employed in combination with complexes of either the (D) or (L) enantiomer of natural amino acids with compounds of formula I may be a thyroid receptor ligand as disclosed in WO97/21993 (U. Cal SF), WO99/00353 (KaroBio) and GB98/284425 (KaroBio), with compounds of the KaroBio applications being preferred.

The anorectic agent which may be optionally employed in combination with complexes of either the (D) or (L) enantiomer of natural amino acids with compounds of formula I may be dexamphetamine, phentermine, phenylpropanolamine or mazindol, with dexamphetamine being preferred.

The various anti-obesity agents described above may be employed in the same dosage form with complexes of either the (D) or (L) enantiomer of natural amino acids with compounds of formula I or in different dosage forms, in dosages and regimens as generally known in the art or in the PDR.

Examples of the anti-platelet agent(s) which may be optionally employed in combinations of this invention include abciximab, ticlopidine, eptifibatide, dipyridamole, aspirin, anagrelide, tirofiban and/or clopidogrel.

Examples of the anti-hypertensive agent(s) which may be optionally employed in combinations of this invention include ACE inhibitors, calcium antagonists, alpha-blockers, diuretics, centrally acting agents, angiotensin-II antagonists, beta-blockers and vasopeptidase inhibitors.

Examples of ACE inhibitors include lisinopril, enalapril, quinapril, benazepril, fosinopril, ramipril, captopril, enalaprilat, moexipril, trandolapril and perindopril; examples of calcium antagonists include amlodipine, diltiazem, nifedipine, verapamil, felodipine, nisoldipine, isradipine and nicardipine; examples of alpha-blockers include terazosin, doxazosin and prazosin; examples of diuretics include hydrochlorothiazide, torasemide, furosemide, spironolactone and indapamide; examples of centrally acting agents include clonidine and guanfacine; examples of angiotensin-II antagonists include losartan, valsartan, irbesartan, candesartan and telmisartan; examples of beta-blockers include metoprolol, propranolol, atenolol, carvedilol and sotalol; and examples of vasopeptidase inhibitors include omapatrilat and gemopatrilat.

In carrying out the method of the invention, a pharmaceutical composition will be employed containing complexes of either the (D) or (L) enantiomer of natural amino acids with compounds of formula I, with or without another antidiabetic agent and/or antihyperlipidemic agent, or other type therapeutic agent, in association with a pharmaceutical vehicle or diluent. The pharmaceutical composition can be formulated employing conventional solid or liquid vehicles or diluents and pharmaceutical additives of a type appropriate to the mode of desired administration. The compounds can be administered to mammalian species including humans, monkeys, dogs, etc. by an oral route, for example, in the form of tablets, capsules, granules or powders, or they can be administered by a parenteral route in the form of injectable preparations. The dose for adults is preferably between 10 and 2,000 mg per day, which can be administered in a single dose or in the form of individual doses from 1–4 times per day.

A typical injectable preparation is produced by aseptically placing 250 mg of a complex of either the (D) or (L) enantiomer of natural amino acids with compounds of formula I into a vial, aseptically freeze-drying and sealing. For use, the contents of the vial are mixed with 2 mL of physiological saline, to produce an injectable preparation.

Figure 2:
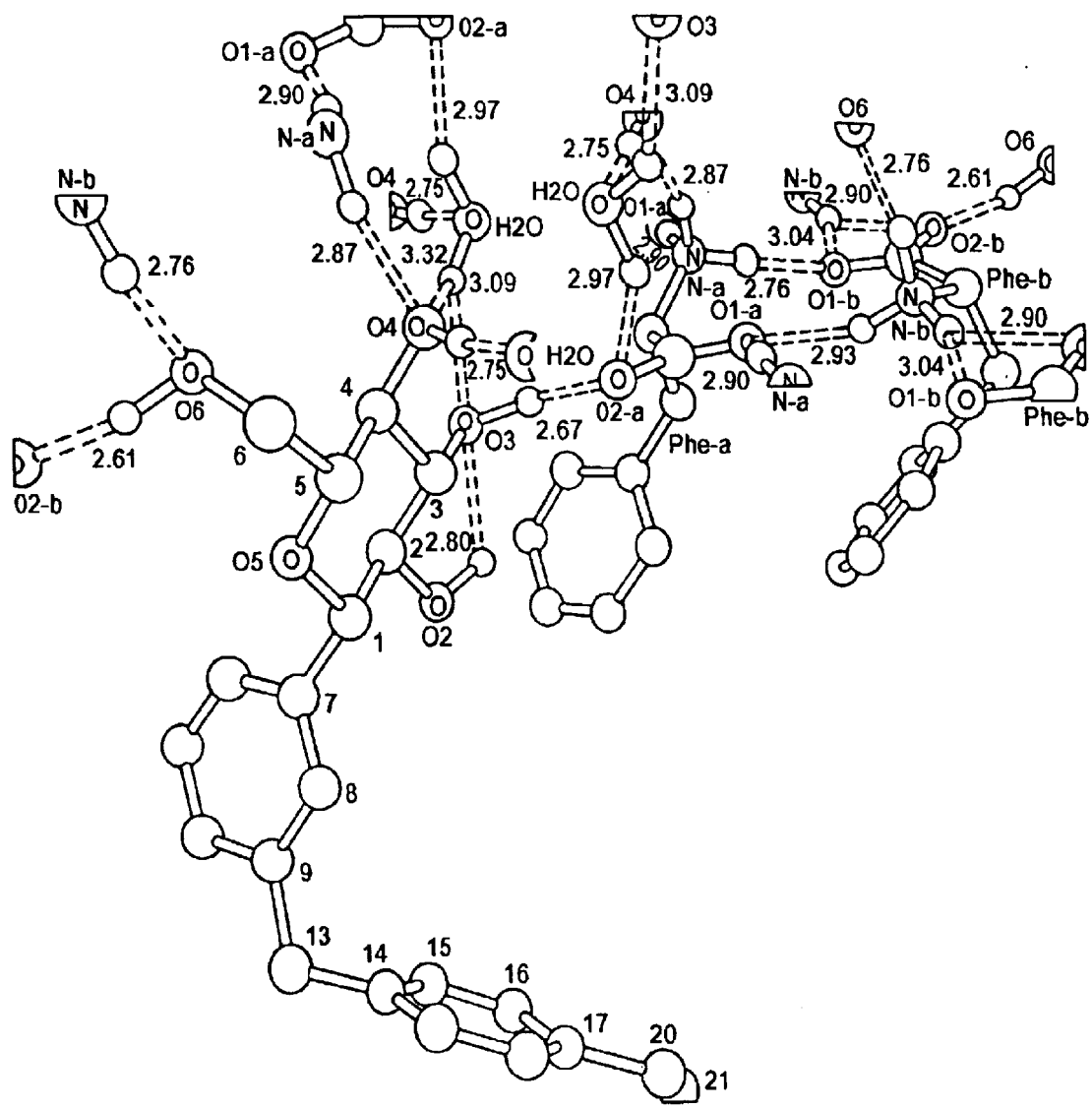
FIG. 2 represents the structure of the 1:2 complex of Compound 3 and L-phenylalanine described in Example 4.
Figure 3:
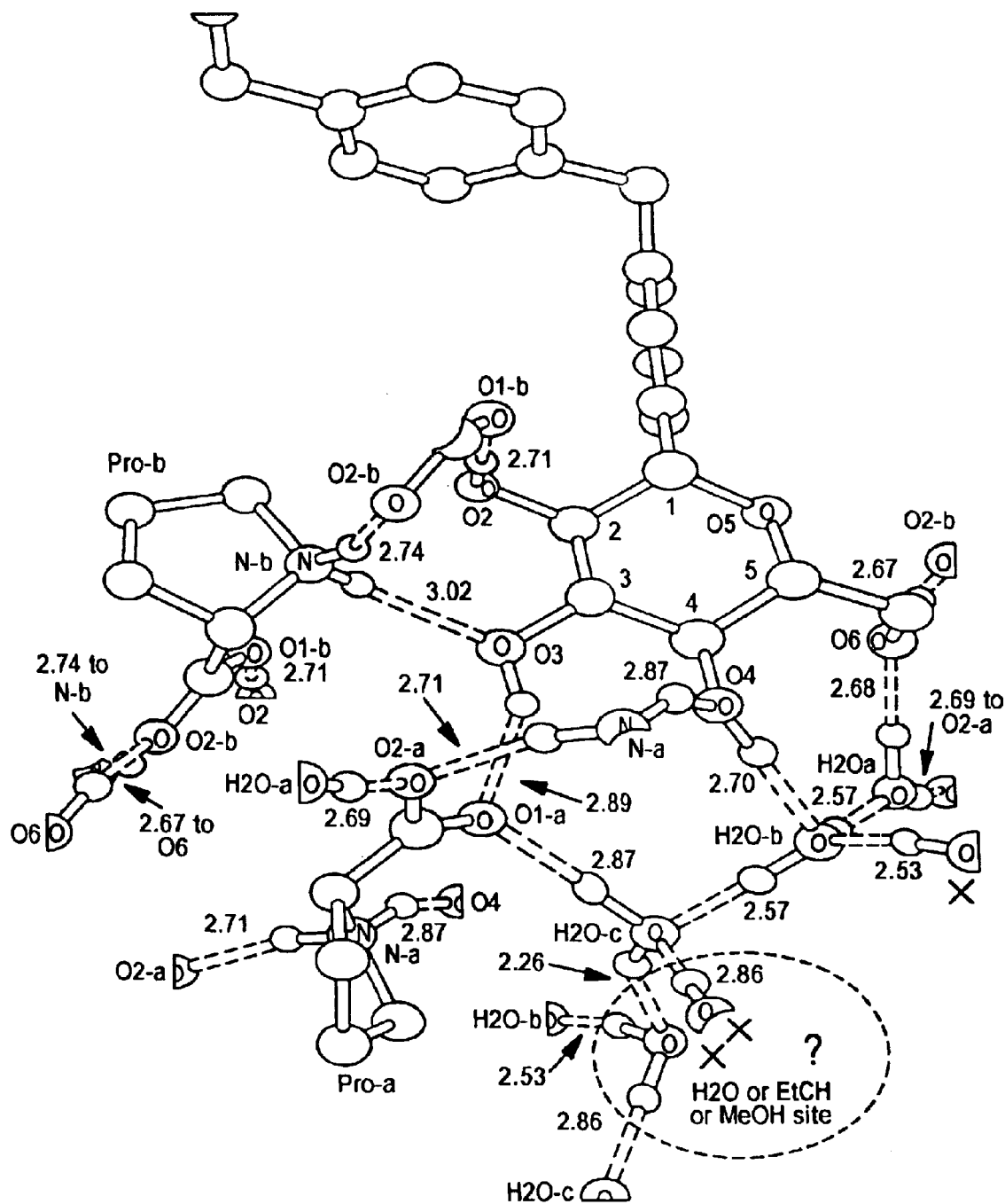
FIG. 3 represents the structure of the 1:2 complex of Compound 3 and L-proline described in Example 5. The dashed circle represents a disorded solvent site that may contain $H_2O$, EtOH or MeOH.
Figure 4:
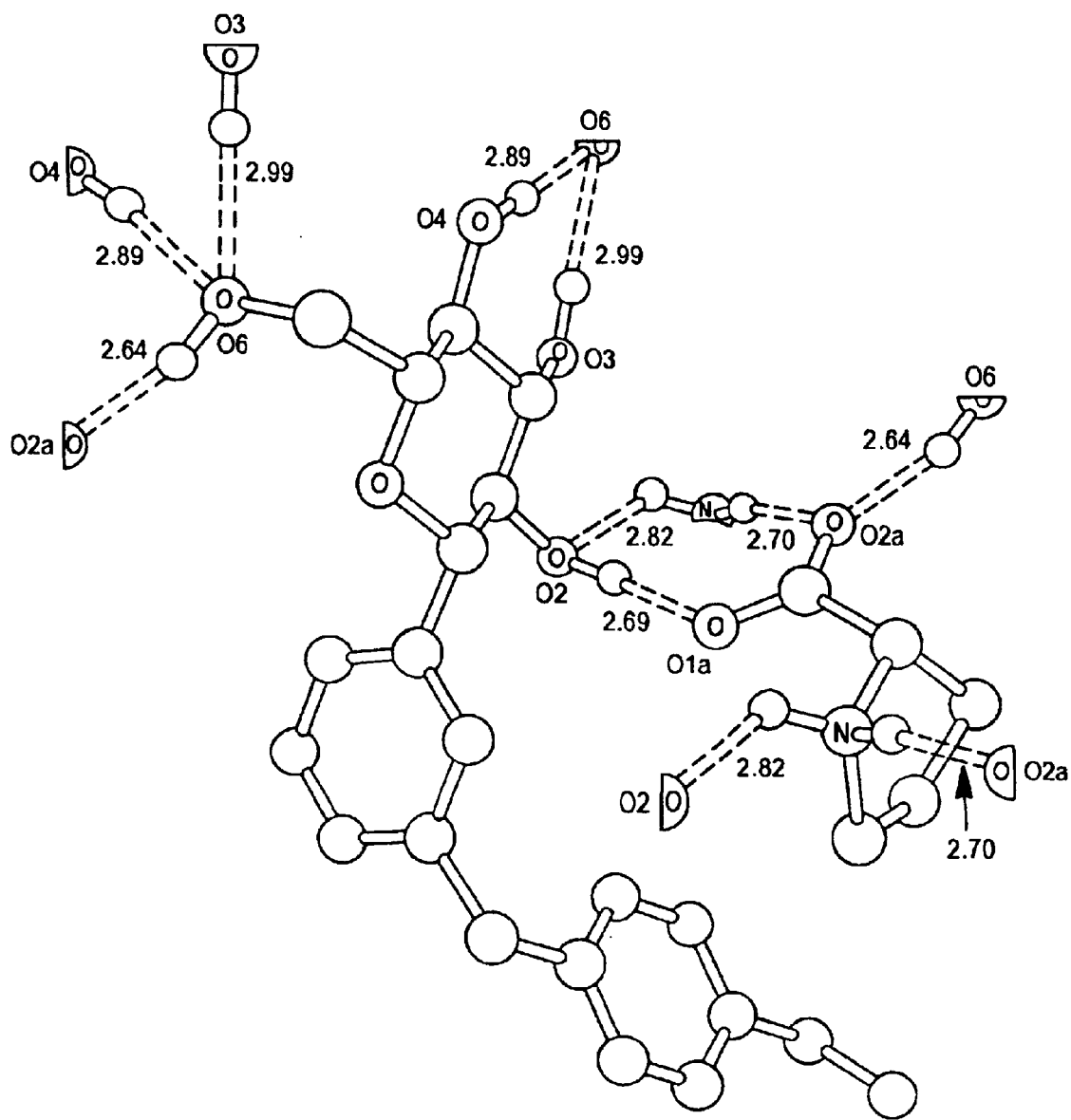
FIG. 4 represents the structure of the 1:12 complex of Compound 3 and L-proline described in Example 6.

The following Working Examples represent preferred embodiments of the present invention. All temperatures are expressed in degrees Centigrade unless otherwise indicated. Crystallographic data as both powder spectra and diffraction patterns obtained fron individual crystals were collected for these complexes. Representative examples of a 1:1 and 1:2 complexes of compounds of formula I with L-phenylalanine are shown in FIGS. 1 and 2. FIGS. 3 and 4 contain representative examples of a 1:1 and 1:2 complexes of compounds of formula I with L-proline. The fractional atomic coordinates for each of these structures are listed in Appendix 1.

EXAMPLE 1

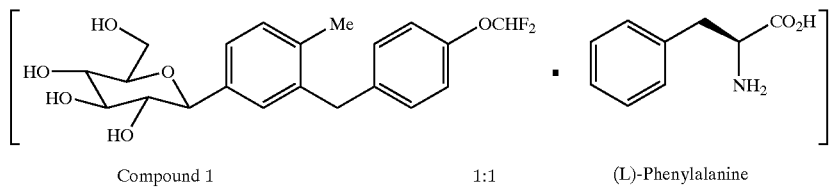

Compound 1     1:1     (L)-Phenylalanine

A. 5-Bromo-2-methylbenzoic Acid

A three neck 2 liter flask, equipped with an overhead stirrer, thermometer, and a dropping funnel having a pressure equalizing sidearm, was charged with o-toluic acid (260 g, 1.89 mol), iron powder (6.74 g, 0.12 mol), and 300 mL of $CH_2Cl_2$. The dropping funnel, after being charged with $Br_2$ (387 g, 2.42 mol), was fitted with a tube that would discharge the effluent gases just above the surface of a stirred 1L solution of 20% NaOH. The temperature of the stirred toluic acid suspension was lowered to 0° whereupon $Br_2$ was added dropwise at such a rate that the addition was complete after 2 hr. At this point the cooling bath was removed and the addition funnel replaced with a reflux condenser to which the effluent gas line was attached in order to continue to trap the effluent HBr gas. The stirred suspension was heated at 40° overnight to drive the reaction to completion. HPLC analysis revealed that the starting toluic acid had been totally consumed and was replaced by two new closely separated peaks with longer retention times in a ~2:1 ratio of 5-bromo- to 3-bromo-2-methybenzoic acids.

The reaction was then quenched by pouring the red suspension into a 4L beaker containing 2L of 10% aq. $NaHSO_3$. The mixture was stirred vigorously for 2–3 hr until all color had been discharged. The solids were collected using a large Buchner funnel. (Note extraction of the filtrate 2× with $CH_2Cl_2$ yielded only a few g of product acid.) The solid was recrystallized at 4° from 95% EtOH to yield 143 g of 99% pure 5-bromo-2-methylbenzoic acid. (Sometimes a $2^{nd}$ recrystallization is required to achieve 99% purity. Concentration of the filtrate will yield a $2^{nd}$ crop of the desired material; note, however, to date efforts to purify by recrystallization a 1:1 mixture of the 3-bromo and 5-bromotoluic acid have failed.)

B. 5-Bromo-2-methyl-4'methoxybenzophenone

To a stirred suspension of Part A 5-bromo-2-methylbenzoic acid (43 g, 200 mmol) in 200 mL of $CH_2Cl_2$ containing oxalyl chloride (140 mL of a 2M $CH_2Cl_2$ solution) was added 0.25 mL of DMF. Once the vigorous evolution of gas ceased, the reaction was stirred 6 hr prior to removal of the volatiles using a rotary evaporator. After dissolving the crude 5-bromo-2-methylbenzoyl chloride in 150 ml of $CS_2$, the resulting solution was cooled to 4° while stirring with an overhead stirrer prior to addition of anisole (21.6 g, 200 mmol) followed by $AlCl_3$ (29.3 g, 220 mmol) in portions. The reaction, after warming to 20° over 1 hr, was stirred for 15 hr prior to quenching by pouring over ice/conc HCl. Subsequently, the suspension was diluted with 500 ml H$_2$O and stirred until all solids were dissolved. The mixture was extracted 3× with EtOAc. The combined organic extracts were washed 1× with 1N HCl, H$_2$O, aq NaHCO$_3$, and brine prior to drying over Na$_2$SO$_4$. After removal of the volatiles, the resulting tan solid was recrystallized from 95% EtOH to yield 55 g of 5-bromo-2-methyl-4'-methoxybenzophenone.

C. 5-Bromo-2-methyl-4'-methoxydiphenylmethane

A solution of Part B 5-bromo-2-methyl-4'-methoxybenzophenone (55 g, 180 mmol), Et$_3$SiH (52 g, 450 mmol), and BF$_3$·Et$_2$O (49 g, 350 mmol) in 350 mL of a 1:4 mixture CH$_2$Cl$_2$/MeCN was stirred overnight at 20°. Since 5% of starting ketone remained by HPLC, the solution was heated to 40° for 1 hr prior to quenching with 10% NaOH. After dilution with H$_2$O, the reaction was extracted 3× with EtOAc. The combined organic layers were washed 2× with H$_2$O and once with brine before drying over Na$_2$SO$_4$. After removal of the volatiles, the residue was chromatographed on silica gel using hexane to elute 5-bromo-2-methyl-4'-methoxydiphenylmethane as a colorless oil (49 g, 95%)

D. 5-Bromo-2-methyl-4'-hydroxydiphenylmethane

To a stirred 300 mL CH$_2$Cl$_2$ solution of Part C$_{-bromo-}$2-methyl-4'-methoxydiphenylmethane (49 g, 170 mmol) at −78° was added 200 mL of a 1M BBr$_3$/CH$_2$Cl$_2$. After 2 hr, the reaction was maintained at −40° for 20 hr whereupon HPLC indicated no starting ether remained. The reaction was quenched with aq. NaOH, extracted 3× with CH$_2$Cl$_2$, washed with brine prior to drying over Na$_2$SO$_4$. After removal of the volatiles, 45 g of 5-bromo-2-methyl-4'-hydroxydiphenylmethane was obtained as a grey solid which was used without further purification.

E. 5-Bromo-2-methyl-4'-t-butyldimethylsiloxy Diphenylmethane

A stirred mixture of Part D 5-bromo-2-methyl-4'-hydroxydiphenylmethane (34 g, 123 mmol) and t-butyldimethylsilylchloride (27.6 g, 180 mmol) in 250 mL CH$_2$Cl$_2$ was cooled to 4° prior to adding DBU (37 g, 245 mmol). After stirring 6 hr at 4°, the reaction stood overnight in a refrigerator at 50 whereupon HPLC analysis showed the reacton to be complete. The reaction was then quenched at 0° by careful addition of sat. NH$_4$Cl. After dilution with H$_2$O, the reaction was extracted 3× with CH$_2$Cl$_2$. The combined CH$_2$Cl$_2$ layers were washed with H$_2$O and brine prior to drying over Na$_2$SO$_4$. The residue, after solvent removal under vacuum was chromatographed on silica gel using 3% EtOAc/hexane to elute 785 mg of 5-bromo-2-methyl-4'-t-butyldimethylsiloxydiphenylmethane as a colorless syrup.

F.

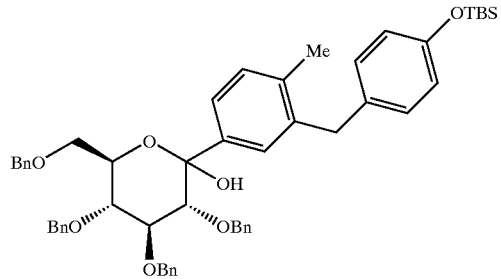

To a stirred −78° solution of Part E 5-bromo-2-methyl-4'-t-butyldimethylsiloxy diphenylmethane (26.6 g, 67.7 mmol) in 100 mL of dry THF under Ar was added 33 mL (75 mmol) of 2.27 M n-BuLi in hexane dropwise. After 60 min, the aryl lithium solution was transferred via cannula to a stirred −78° solution of 2,3,4,6-tetra-O-benzyl-β-D-glucolactone (40.1 g, 74 mmol) in 50 mL of THF. The reaction was stirred for 4 hr at −78° prior to quenching with saturated aq. NH$_4$Cl. After warming to 20°, the reaction was diluted 2 fold with H$_2$O prior to 3 extractions with EtOAc. The combined EtOAc fractions were washed with brine and dried over Na$_2$SO$_4$. After concentration using a rotary evaporator, 68 g of crude lactol was obtained as a yellow syrup. Chromatography on 1.3 kg of silica gel using 1:6 EtOAc/hexane eluted 32.5 g of pure desired title lactol plus another 12 g of impure product.

G.

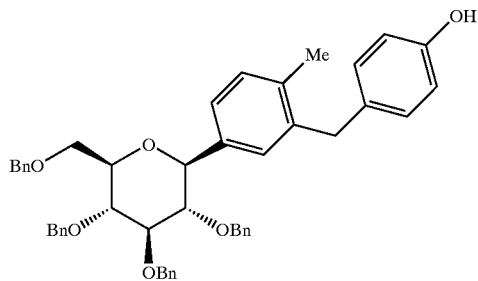

To a stirred −40° solution of Part F lactol (30.4 g, 35.8 mmol) in 100 mL of dry MeCN was added iPr$_3$SiH (7.3 g, 46 mmol) followed by gradual addition of BF$_3$·Et$_2$O (6.1 g, 43 mmol). After stirring the resulting yellow solution 3 hr at −40°--−30°, a second portion of iPr$_3$SiH (1.3 g, 8 mmol) and BF$_3$·Et$_2$O (1 g, 7 mmol) was added. After an additional 4 hr at −40°, tlc analysis showed no remaining lactol. Saturated aq. K$_2$CO$_3$ was added and the suspension stirred 1 hr at 200 prior to diluting with H$_2$O and EtOAc. The combined organic layers from 3 EtOAc extractions were washed with brine, dried over Na$_2$SO$_4$, and concentrated using a rotary evaporator to yield 33.5 g of a light yellow syrup. Chromatography on silica gel with 9% EtOAc/hexane eluted nonpolar impurities; 1:3 EtOAc/hexane eluted the desired beta C-arylglucoside (23 g) which formed a white solid upon isolation.

H.

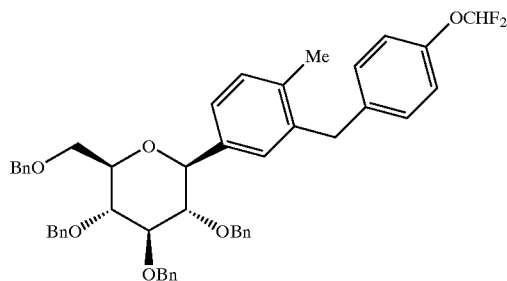

A solution of Part G tetrabenzyl-phenolic C-glucoside (23 g, 30 mmol) in iPrOH (200 mL) in a glass insert was cooled to −60°. A −40° aq. KOH solution (previously prepared by dissolving 50 g KOH in 75 mL H$_2$O) was added. To this −60° mixture was added by cannula 150 g of liquid CHF$_2$Cl (Freon 22). The cold insert was quickly placed into a stainless steel bomb (chilled to −−20°) equipped with a pressure gauge, thermocouple probe, two motor driven propellers mounted one above the other for efficient stirring. After sealing the bomb, the assembly was placed into its heater. Stirring was begun and the heater turned on. Pressure was monitored as a function of temperature. Due to external heating, the temperature slowly rose to +32; concurrently the pressure increased to 50 psi. At this point the reaction initiated sending the temperature to 72° and pressure to 200 psi over a two minute period. (This effect was reproduced on four subsequent occcasions always starting at 32°). The heater was turned off; stirring was continued for another 2 hr. The bomb was recooled to −40° whereupon the vent, after being fitted with a line leading to a flask at −78° to trap the gases, was opened. A small amount of very low boiling gas (tetrafluoroethylene?) exited first followed by residual Freon as the bomb temperature warmed to 30°. Typically 20 g of Freon was recovered which could be recycled. After the gases had been removed, the insert was taken out, the desired product (poorly soluble in iPrOH) formed a third phase intermediate in density between the iPrOH and aq layer (pH ~8 with precipitated salts) The iPrOH layer was separated and the volatiles removed using a rotary evaporater. Both this residue and the oily product layer were dissolved in EtOAc. After three EtOAc extractions of the aqueous layer, the combined EtOAc layers were washed with brine, dried over $NaSO_4$ prior to removal of the volatiles. By HPLC, the conversion of phenol to desired product was 95%. The crude product was purified by chromatography using 1:7 EtOAc to elute 18 g of the tetrabenzylated difluoromethyl ether.

I.

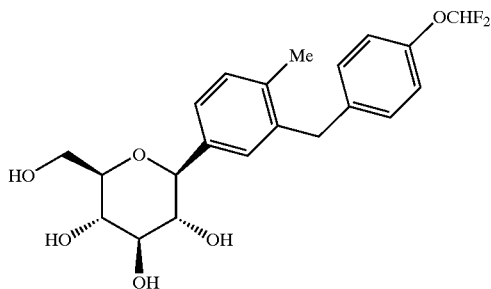

To a stirred solution of Part H tetrabenzylated difluoromethyl ether (23 g) in 225 mL of EtOAc in a 500 mL round bottom flask was added 2.3 g of 10% $Pd(OH)_2/C$. The reaction was stirred for 24 hr under 1 atmos. $H_2$. After HPLC showed the reaction to be complete, the catalyst was filtered using celite and the solvent removed using a rotary evaporator to obtain 12 g of a white glassy solid containing 2–3% of minor impurities by HPLC. Further purification was achieved by silica gel chromatography using 5–9% MeOH/$CH_2Cl_2$ to elute 10.7 g of Compound 1.

J.

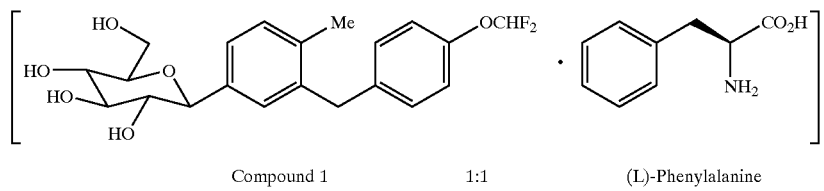

Compound 1  1:1  (L)-Phenylalanine

A solution of Part I compound 1 (55 mg, 0.13 mmol), prepared by dissolution in 0.3 mL of ethanol upon heating to 55°, was transferred to a stirred 50° solution comprised of (L)-phenylalanine (22 mg, 0.13 mmol) in 0.9 mL $H_2O$. After mixing was complete, stirring was stopped and the solution was allowed to cool to 20° over 6 hr. (Seed crystals can be added to aid crystal formation.) After 24 hr small white needles were isolated by filtration, washed 3× with cold 25% ethanol/$H_2O$, and air dried.

EXAMPLE 2

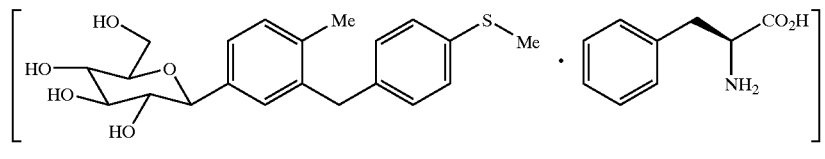

Compound 2  1:1  (L)-Phenylalanine

A. 5-Bromo-2-methyl-4'-thiomethylbenzophenone

A stirred suspension of 5-bromo-2-methylbenzoic acid (90 g, 0.42 mol) (preparation described in Part A of Example 1) in 700 mL of $CH_2Cl_2$ in a 3-neck 2L flask equipped with a mechanical stirrer was cooled to 4° in an ice bath. Using an addition funnel, 272 mL of a 2M oxalyl chloride (0.56 mol) in $CH_2Cl_2$ was added over 10 min followed by pipette addition of 1 mL of DMF. The suspension was stirred for 15 min whereupon the bath was removed and the stirred reaction warmed to 20°. Copious gas began to evolve as the reaction progressively became homogeneous when stirred for 3 hr. (Warming to 35° accelerates this process.) Filtration through a glass frit to remove of any residual solid and subsequent concentration using a rotary evaporator yielded the desired acid chloride as a viscous golden oil.

The crude acid chloride in 600 mL of $CS_2$ was transferred to a 3 neck 2L flask equipped with a mechanical stirrer and thermometer; thioanisole (50 mL, 0.42 mol) was added and the solution cooled to 0°. $AlCl_3$ (75 g, 0.56 mol) was added in portions at a rate to maintain the temperature of the stirred reaction below 5°. After 3 hr the bath was removed and the mixture stirred overnight. The reaction was checked by HPLC prior to quenching; if not complete additional thioanisole and $AlCl_3$ were added to drive it to completion. Quenching entailed pouring the contents onto 1.5 L of ice containing 50 mL of conc HCl and stirring vigorously for 2 hr until all solids were in solution. The mixture was extracted 2× with $CH_2Cl_2$. The combined organic extracts were washed 1× with 1N HCl, H₂O, aq NaHCO₃, and brine prior to drying over Na₂SO₄. After removal of the volatiles using a rotary evaporator, the crude solid (118 g) was recrystallized from 300 mL of EtOH with the aid of seed crystals to yield 94 g (97.5% purity by HPLC) of 5-bromo-2-methyl-4'-thiomethylbenzophenone as a white solid.

B. 5-Bromo-2-methyl-4'-thiomethyldiphenylmethane

To a stirred solution of Et₃SiH (103 mL, 0.64 mol) and Part B 5-bromo-2-methyl-4'-thiomethylbenzophenone (94 g, 0.29 mol) in 2L of MeCN at 40 was added dropwise BF₃·Et₂O (82 mL, 0.64 mol). After 30 min, the bath was removed and the solution stirred overnight at 20°. The reaction was checked by HPLC prior to quenching; if not complete additional Et₃SiH and BF₃·Et₂O were added to drive it to completion. Following quenching with 10% NaOH and dilution with H₂O, the reaction was extracted 2× with Et₂O (1L split in two portions). The combined organic layers were washed 10 to 15× with H₂O (500 mL portions) until no Et₃SiX signals could be discerned by ¹H NMR analysis of aliquots. The solution was then extracted with brine 1× before drying over Na₂SO₄ prior to removal of the volatiles using a rotary evaporator to yield 79.5 g of 5-bromo-2-methyl-4'-thiomethyldiphenylmethane as a white solid. Small portions of this material were recrystallized successfully from absolute EtOH however oiling out was a persistent problem on a large scale. Typically this aryl bromide, after purity was confirmed by ¹H NMR and HPLC, was azeotroped twice using toluene and then used directly in the subsequent step.

C.

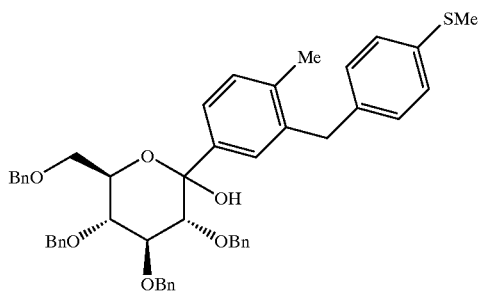

To a stirred −78° solution of Part B 5-bromo-2-methyl-4'-thiomethyldiphenylmethane (200 mg, 0.65 mmol) in 10 mL of dry THF under Ar was added dropwise 0.42 mL of 1.8 M n-BuLi in hexane. After 2 hr, this solution was transferred by cannula to a stirred −78° solution of 2,3,4,6-tetra-O-benzyl-β-D-glucolactone (0.88 g, 1.6 mmol) in 5 mL of THF. The solution was stirred for 2 hr at −78° before quenching with saturated aq. NH₄Cl. After warming to 20°, the reaction was diluted 2 fold with H₂O prior to 3 extractions with EtOAc. The combined EtOAc fractions were washed with brine and dried over Na₂SO₄. After concentration using a rotary evaporator, 550 mg of the desired title lactol was obtained as a colorless syrup that was carried forward without further purification.

D.

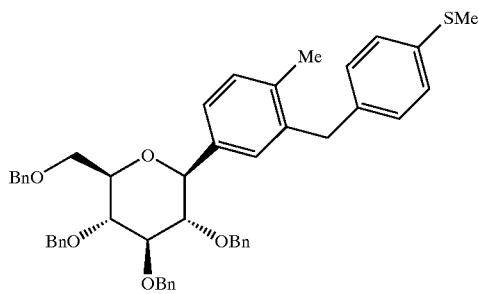

To a stirred −40° solution of Part C lactol (550 mg, 0.72 mmol) in 6 mL of MeCN was added iPr₃SiH (0.22 mL, 1.0 mmol) followed by BF₃·Et₂O (0.11 mL, 0.8 mmol). After 1.5 hr at −40°—−30°, when tlc showed the reaction to be complete, saturated aq. K₂CO₃ was added and the suspension stirred 1 hr at 20° prior to diluting with H₂O and EtOAc. The combined organic layers from 3 EtOAc extractions were washed with brine, dried over Na₂SO₄, and concentrated using a rotary evaporator. Chromatography of the residue on silica gel using 9% EtOAc/hexane as eluant eluted 240 mg of the desired beta C-arylglucoside.

E.

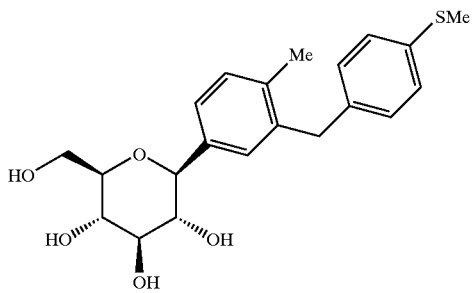

A solution of Part D tetra-O-benzyl C-glucoside (70 mg, 0.1 mmol) in EtSH (1.5 mL) containing BF₃·Et₂O (0.24 mL, 2 mmol) was stirred at 20° for 2 hr. After 1 more hr following addition of an additional 0.12 mL of BF₃·Et₂O, the reaction was complete. The reaction was quenched by slow addition of 0.4 mL of pyridine prior to dilution with aq. NH₄Cl. The combined organic layers from 3 EtOAc extractions were washed with brine, dried over Na₂SO₄, and concentrated using a rotary evaporator. The residue was purified by preparative HPLC using a C₁₈ reverse phase column to obtain 20 mg of compound 2 as a white lyophilate after lyophilization.

F.

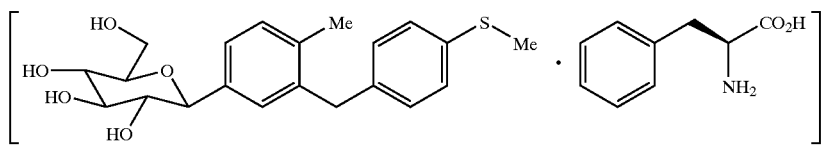

Compound 2     1:1     (L)-Phenylalanine

A solution of compound 2 (55 mg, 0.13 mmol), prepared by dissolution in 0.3 mL of ethanol upon heating to 55°, was transferred to a stirred 500 solution comprised of (L)-phenylalanine (22 mg, 0.13 mmol) in 0.9 mL $H_2O$. After mixing was complete, stirring was stopped and the solution was allowed to cool to 20° over 6 hr. (Seed crystals can be added to aid crystal formation.) After 24 hr small white needles were isolated by filtration, washed 3× with cold 25% ethanol/$H_2O$, and air dried.

EXAMPLE 3

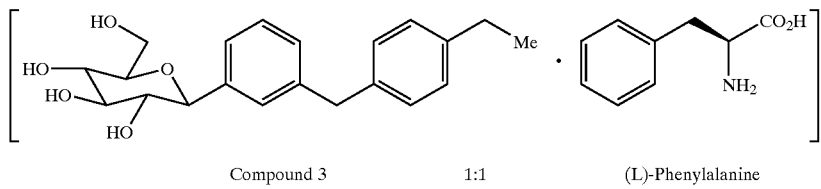

Compound 3    1:1    (L)-Phenylalanine

A. 3-Bromo-4'-ethylbenzylhydrol

Dry Mg turnings (4.4 g, 0.178 mol) under Ar were stirred overnight whereupon 100 mL of dry $Et_2O$ was added followed by addition over 1 hr of p-bromoethylbenzene (22 g, 0.119 mol) in 20 mL of $Et_2O$. (In the event the reaction did not start, 0.5 ml of 1,2-dibromoethane was added). After stirring overnight, m-bromobenzaldehyde (11 g, 0.06 mol) in 20 mL of $Et_2O$ was slowly added. The resulting light solution was monitored by HPLC over 4–6 hr to determine when complete. The reaction, after quenching with saturated aq. $NH_4Cl$, was extracted 3× with EtOAc. The combined organic layers were washed with brine, dried over $Na_2SO_4$ and concentrated using a rotary evaporator. The resulting yellow oil was chromatographed on silica gel using 5% EtOAc/hexane to elute nonpolar impurities and 7–9% EtOAc/hexane to elute 12.4 g (71%) of 3-bromo-4'ethylbenzhydrol as a light yellow oil.

B. 3-Bromo-4'-ethyldiphenylmethane

To a stirred −30° solution of Part A 3-bromo-4'-ethylbenzhydrol (12.4 g, 0.0426 mol) in 120 mL of MeCN was added $BF_3·Et_2O$ (6.04 g, 0.0426 mol) followed by $Et_3SiH$ (9.9 g, 0.852 mol). The dark reaction after stirring 1 hr at −30° was warmed slowly to −50. When complete by tlc, the reaction was quenched by addition of saturated aq. $K_2CO_3$. After addition of 100 mL of $H_2O$, the mixture was extracted 3× with $Et_2O$. The combined organic layers were washed with brine, dried over $Na_2SO_4$. After concentration using a rotary evaporator, 3-bromo-4'-ethyldiphenylmethane (11.17 g, 95%) was obtained as a light yellow oil that was used without further purification.

C.

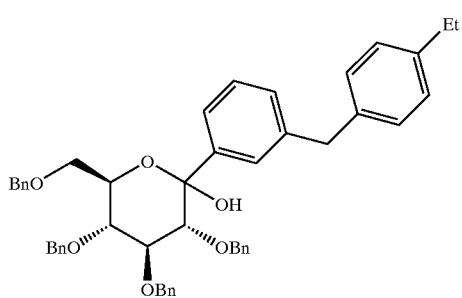

To a stirred −78° solution of Part B 3-bromo-4'-ethyldiphenylmethane (10.9 g, 0.04 mol) in 100 mL of dry THF under Ar was added 25.7 mL of 1.7 M t-BuLi in hexane over 20 min. After 1 hr 2,3,4,6-tetra-O-benzyl-β-D-glucolactone (23.5 g, 0.0437 mol) in 30 mL of THF was added over 15 min. The solution was stirred for 1 hr at −78° prior to quenching with saturated aq. $NH_4Cl$. After warming to 20°, the reaction was diluted 2 fold with EtOAc prior to washing with $H_2O$ followed by brine. After drying over $Na_2SO_4$ and concentration using a rotary evaporator, 29.2 g of the desired title lactol was obtained as a colorless syrup that was carried forward without further purification.

D.

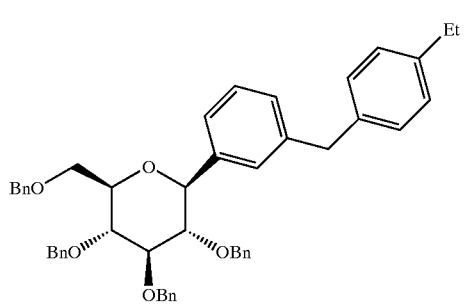

To a stirred −30° solution of Part C lactol (29.1 g, 0.04 mol) in 100 mL of MeCN was added $BF_3·Et_2O$ (5.62 g, 0.04 mol) followed by $Et_3SiH$ (9.21 g, 0.08 mol). After 2 hr, when tlc showed the reaction to be complete, saturated aq. $K_2CO_3$ was added and the suspension stirred 1 hr at 20° prior to diluting with $H_2O$ and $Et_2O$. The combined organic layers from 3 $Et_2O$ extractions were washed with brine, dried over $Na_2SO_4$, and concentrated using a rotary evaporator to yield 28.3 g of a light yellow syrup. Chromatography on silica gel with 5% EtOAc/hexane eluted nonpolar impurities followed slowly by the desired beta anomer and then the alpha anomer. Fractions enriched in the beta anomer could be further purified by either triterating with hexane or by recrystalization from EtOH to yield 6 g of the desired title beta tetra-O-benzyl C-glucoside. (Note when $Et_3SiH$ is the reducing agent, a 5:1 beta/alpha anomer mixture is obtained whereas when $iPr_3SiH$ is substituted a 30:1 mixture is obtained.)

E.

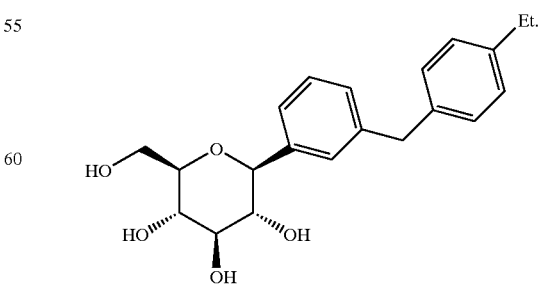

A solution of Part D tetra-O-benzyl C-glucoside (2.4 g, 3.35 mmol) in EtOAc (100 mL) containing 10% $Pd(OH)_2/C$ (0.35 g) was stirred overnight under 1 atmos. H$_2$. After HPLC showed the reaction to be complete, the catalyst was filtered and the solvent removed using a rotary evaporator to obtain 1.1 g of the desired beta C-glucoside Compound 3 as a white glassy solid in 92% yield.

F.

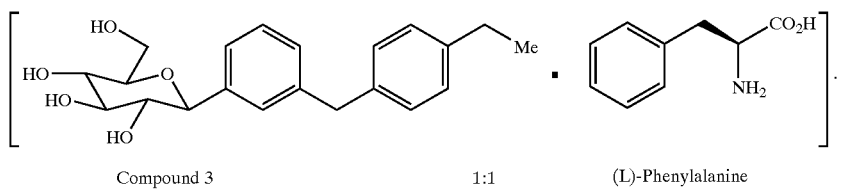

Compound 3  1:1  (L)-Phenylalanine

A solution of Part E compound 3 (5 g, 0.13 mmol), prepared by dissolution in 7 mL of ethanol upon heating to 60°, was quickly transferred to a stirred 80° solution comprised of (L)-phenylalanine (2.23 g, 0.13 mmol) and 89.2 mL of H$_2$O. After mixing was complete, stirring was continued at 80° until the solution was clear. The stirred solution was cooled to ~60° over ~10 min whereupon a milky white suspension began to form. Upon each 2° drop in temperature, seed crystals were added in small amounts to promote crystalization which normally began at 52°. The suspension was then cooled to 40° and stirred for 4 hr. Subsequently, the temperature was lowered to 22° over 2 hr and then stirred for another 3 hr. Finally the temperature was decreased to 18° followed by stirring for 2 hr. Small white needles, after isolation by filtration, were washed 2× with 12.5 mL of ice H$_2$O and 2× with 12.5 mL of t-BuOMe before drying at 40°.

EXAMPLE 4

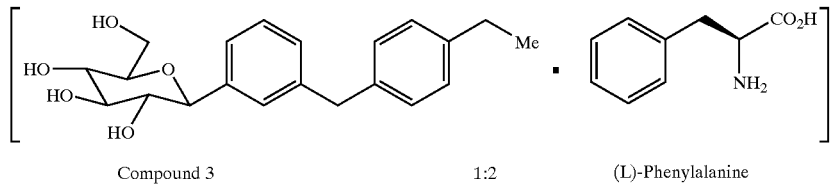

Compound 3  1:2  (L)-Phenylalanine

To a solution of compound 3 (5 g, 0.13 mmol) dissolved in 30 mL of ethanol was added 32 mL of H$_2$O followed by (L)-phenylalanine (4.2 g, 0.13 mmol). The suspension was heated with stirring at 80° until the solution became clear. The solution was slowly cooled to ~20° over ~2 hr. Crystalization began at ~40–45°. After standing for 6 hr at 20°, small white needles, after isolation by filtration, were washed 1× with 20 mL of ice H$_2$O and 1× with 20 mL of t-BuOMe before drying at 40°.

EXAMPLE 5

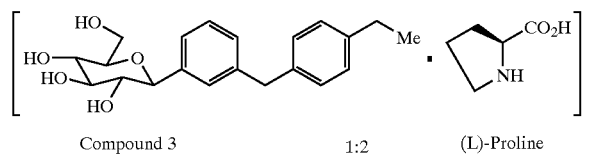

Compound 3  1:2  (L)-Proline

To a 25° solution of compound 3 (1.06 g, 3.0 mmol) dissolved in 2 mL of ethanol was added 2.2 mL of a 1:10H$_2$O/EtOH solution at 250 containing (L)-proline (0.69 g, 6.0 mmol) which had been previously prepared by stirring while gently warming. Following addition of a 0.5 mL EtOH rinse of the flask containing the proline solution, a paste immediately formed. The paste was transferred to a sintered glass funnel, pressed to expel as much solvent as possible, and subsequently washed with 3× with 1 mL portions of EtOH. After drying under vacuum for 15 hr, 1.68 g of the title complex was obtained.

EXAMPLE 6

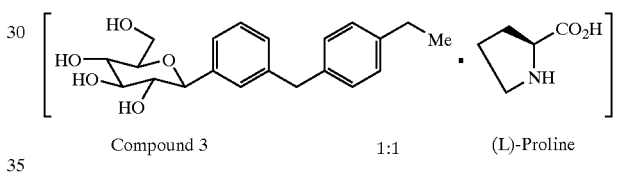

Compound 3  1:1  (L)-Proline

Seed crystals for the 1:1 proline/glucoside complex were prepared by stirring the 2:1 proline/glucoside complex (300 mg) described in Example 5 in MeOH (1 mL) for 72 hr at 20°. The resulting slurry was filtered using centrifugation to provide a solid with m.p. of 162–163°.

A mixture of compound 3 (312 mg, 0.87 mmol) and L-proline (100 mg, 0.87 mmol) was heated to 600 in 1.55 mL of 1:30 H$_2$O/EtOH for a few minutes until the solution was homogeneous. After cooling the solution to 50°, ~1 mg of the 1:1 seed crystals were added. The solution was transformed into a thick white slurry over a period of 1 hr at 50°. The mixture was cooled to 40° over 1 hr prior to addition over 30 min of 2.5 mL of heptane with stirring. The temperature of the slurry was lowered to 20° over 1 hr; whereupon, the fine needles were collected by filtration to yield the title complex in 83% yield after drying.

EXAMPLE 7

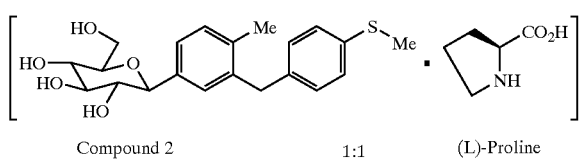

Compound 2                    1:1                    (L)-Proline

To a solution of compound 2 (500 mg, 1.13 mmol), prepared by dissolution in 3 mL of iPrOH upon heating to 35°, was added a 60° solution of (L)-proline (147 mg, 1.13 mmol) in 7 mL of absolute EtOH. The resulting combination was heated with stirring at 60° until homogeneous whereupon the stirring was stopped and the solution was allowed to cool to 200 over 6 hr. After 24 hr small white needles were isolated by filtration, washed 3× with cold 2:1 ethanol/iPrOH, and air dried. MP 195°.

EXAMPLE 8

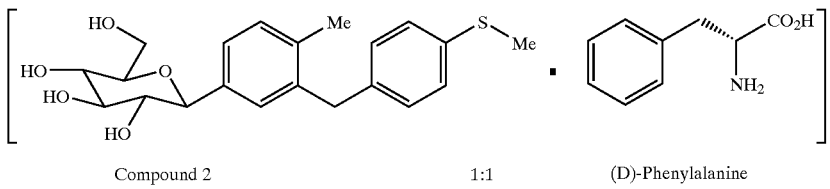

Compound 2                    1:1                    (D)-Phenylalanine

A stirred suspension of compound 2 (200 mg, 0.47 mmol) and (D)-phenylalanine (84.6 mg, 0.47 mmol) in 2.7 mL $H_2O$ and 1.3 mL of 95% ethanol was heated at 80° until homogeneous. The solution was filtered prior to to be allowed to cool slowly to 20° over 6 hr. (Seed crystals can be added to aid crystal formation.) After 24 hr small white needles were isolated by filtration, washed 3× with cold 25% ethanol/$H_2O$, and air dried to yield 220 mg of the desired 1:1 complex. MP 188°.

| Complex | Space Group | Unit Cell Volume | Comments |
|---|---|---|---|
| Example 1 | $P2_1$ | 1455 | |
| Example 2 | | | Unstable Solvate |
| Example 3 | | | Too small crystals |
| Example 4 | $P2_1$ | 1799 | |
| Example 5 | $P2_1$ | 1704 | |
| Example 6 | $P2_12_12_1$ | 621 | |
| Example 7 | | | Too small crystals |
| Example 8 | | | |

TABLE 1

Fractional Atomic Coordinates for the 1:1 L-phenylalanine compound 1 complex described in Example 1

| Atom | x | y | z | B(A2) |
|---|---|---|---|---|
| O2 | 0.801(1) | 0.290(3) | 0.6893(6) | 3.2(3) |
| O3 | 0.890(1) | 0.592(3) | 0.5920(6) | 3.2(3) |
| O4 | 1.073(1) | 0.391(2) | 0.5141(5) | 2.5(2) |
| O5 | 1.0926(9) | 0.096(2) | 0.6677(5) | 2.2(2) |
| O6 | 1.288(1) | −0.078(3) | 0.6110(6) | 3.3(3) |
| O20 | 0.344(1) | −0.337(4) | 0.9313(8) | 6.4(4) |

TABLE 1-continued

Fractional Atomic Coordinates for the 1:1 L-phenylalanine compound 1 complex described in Example 1

| Atom | x | y | z | B(A2) |
|---|---|---|---|---|
| F1 | 0.215(1) | −0.256(4) | 1.0006(8) | 10.0(5) |
| F2 | 0.288(2) | 0.002(5) | 0.9440(9) | 10.8(6) |
| O40 | 0.500(1) | 0.507(3) | 0.5458(6) | 3.8(3) |
| O41 | 0.627(1) | 0.345(2) | 0.6074(5) | 2.6(3) |
| N42 | 0.529(1) | 0.921(3) | 0.5865(6) | 2.1(3) |
| O | 0.733(1) | 0.127(3) | 0.5010(6) | 4.0(3) |
| C1 | 0.972(1) | 0.077(3) | 0.6836(8) | 2.1(3) |
| C2 | 0.916(1) | 0.305(3) | 0.6697(8) | 2.3(4) |
| C3 | 0.937(1) | 0.365(3) | 0.6015(8) | 2.2(4) |
| C4 | 1.062(1) | 0.363(3) | 0.5815(8) | 1.9(3) |
| C5 | 1.114(1) | 0.134(3) | 0.5999(8) | 2.0(3) |
| C6 | 1.241(2) | 0.141(4) | 0.5891(9) | 2.8(3) |
| C7 | 0.961(1) | 0.007(4) | 0.7521(8) | 2.3(4) |
| C8 | 0.891(1) | −0.185(3) | 0.7683(8) | 2.1(4) |
| C9 | 0.879(2) | −0.256(4) | 0.8312(9) | 2.5(4) |
| C10 | 0.940(2) | −0.167(4) | 0.8778(9) | 3.0(4) |

TABLE 1-continued

Fractional Atomic Coordinates for the 1:1 L-phenylalanine compound 1 complex described in Example 1

| Atom | x | y | z | B(A2) |
|---|---|---|---|---|
| C11 | 1.008(2) | 0.034(4) | 0.8614(9) | 3.3(4) |
| C12 | 1.017(2) | 0.108(4) | 0.8008(9) | 2.7(4) |
| C13 | 0.804(2) | −0.478(4) | 0.8420(9) | 2.9(4) |
| C14 | 0.683(2) | −0.423(4) | 0.8648(9) | 2.7(4) |
| C15 | 0.599(2) | −0.587(5) | 0.858(1) | 4.1(5) |
| C16 | 0.491(2) | −0.551(5) | 0.880(1) | 4.5(5) |
| C17 | 0.458(2) | −0.356(4) | 0.9122(9) | 3.7(5) |
| C18 | 0.539(2) | −0.190(5) | 0.918(1) | 4.8(5) |
| C19 | 0.650(2) | −0.217(4) | 0.895(1) | 3.7(5) |
| C22 | 0.935(2) | −0.238(5) | 0.946(1) | 4.7(5) |
| C31 | 0.601(2) | 0.748(4) | 0.6175(9) | 3.0(4) |
| C32 | 0.593(2) | 0.764(4) | 0.6877(8) | 2.5(4) |
| C33 | 0.480(1) | 0.742(3) | 0.7169(8) | 2.3(4) |
| C34 | 0.407(2) | 0.547(4) | 0.7108(9) | 3.3(4) |
| C35 | 0.297(2) | 0.530(5) | 0.736(1) | 4.0(5) |
| C36 | 0.249(2) | 0.730(5) | 0.770(1) | 4.6(5) |
| C37 | 0.320(2) | 0.905(5) | 0.778(1) | 4.1(5) |
| C38 | 0.425(2) | 0.919(5) | 0.7510(9) | 3.3(4) |
| C39 | 0.572(1) | 0.518(4) | 0.5847(8) | 2.1(3) |
| C21 | 0.325(2) | −0.194(6) | 0.980(1) | 6.5(7) |
| Hydrogen Atoms (not refined) | | | | |
| H11 | 0.935 | −0.039 | 0.653 | 3.1*— |
| H21 | 0.957 | 0.448 | 0.698 | 3.4*— |
| H31 | 0.895 | 0.253 | 0.572 | 3.6*— |
| H41 | 1.103 | 0.516 | 0.605 | 3.3*— |
| H51 | 1.076 | 0.010 | 0.573 | 3.4*— |
| H61 | 1.265 | 0.175 | 0.540 | 4.1*— |
| H62 | 1.275 | 0.290 | 0.617 | 4.1*— |
| H81 | 0.845 | −0.261 | 0.730 | 3.5*— |
| H111 | 1.055 | 0.127 | 0.899 | 4.8*— |
| H121 | 1.072 | 0.262 | 0.789 | 4.1*— |
| H131 | 0.804 | −0.567 | 0.798 | 4.8*— |
| H132 | 0.843 | −0.577 | 0.878 | 4.8*— |

TABLE 1-continued

Fractional Atomic Coordinates for the 1:1 L-phenylalanine compound 1 complex described in Example 1

| Atom | x | y | z | B(A2) |
|---|---|---|---|---|
| H151 | 0.623 | −0.740 | 0.835 | 6.0* |
| H161 | 0.428 | −0.668 | 0.871 | 5.7* |
| H181 | 0.516 | −0.025 | 0.948 | 6.3* |
| H191 | 0.714 | −0.069 | 0.902 | 5.9* |
| H221 | 0.995 | −0.126 | 0.973 | 6.3* |
| H222 | 0.853 | −0.218 | 0.967 | 6.3* |
| H223 | 0.966 | −0.406 | 0.948 | 6.3* |
| H211 | 0.388 | −0.227 | 1.012 | 8.6* |
| H311 | 0.688 | 0.798 | 0.599 | 3.8* |
| H321 | 0.649 | 0.644 | 0.707 | 3.8* |
| H322 | 0.631 | 0.941 | 0.701 | 3.8* |
| H341 | 0.443 | 0.399 | 0.682 | 4.7* |
| H351 | 0.249 | 0.379 | 0.730 | 5.3* |
| H361 | 0.162 | 0.720 | 0.789 | 6.5* |
| H371 | 0.287 | 1.049 | 0.805 | 5.5* |
| H381 | 0.475 | 1.065 | 0.757 | 5.3* |
| H02 | 0.753 | 0.311 | 0.651 | 4.9* |
| H06 | 1.263 | −0.106 | 0.656 | 5.3* |
| H04 | 1.148 | 0.474 | 0.503 | 3.6* |
| H03 | 0.902 | 0.633 | 0.545 | 4.8* |
| H421 | 0.536 | 0.912 | 0.539 | 3.7* |
| H442 | 0.447 | 0.892 | 0.600 | 3.7* |
| H423 | 0.550 | 1.078 | 0.600 | 3.7* |
| H1 | 0.692 | 0.213 | 0.536 | 5.7* |
| H2 | 0.723 | 0.223 | 0.463 | 5.7* |

Starred atoms were not refined.

TABLE 2

Fractional Atomic Coordinates for the 2:1 L-phenylalanine compound 3 complex described in Example 4

| Atom | x | y | z | B(A2) |
|---|---|---|---|---|
| Hydrogen Atoms (not refined) | | | | |
| H51 | 0.704 | −0.049 | 0.623 | 3.3* |
| H41 | 0.754 | 0.463 | 0.595 | 3.1* |
| H31 | 0.621 | 0.256 | 0.667 | 3.5* |
| H11 | 0.738 | 0.025 | 0.734 | 3.2* |
| H61 | 0.742 | −0.056 | 0.521 | 3.6* |
| H62 | 0.830 | −0.170 | 0.578 | 3.6* |
| H21 | 0.790 | 0.539 | 0.709 | 3.7* |
| H131 | 0.989 | −0.174 | 0.975 | 4.9* |
| H132 | 0.963 | −0.398 | 0.915 | 4.9* |
| H101 | 1.058 | 0.108 | 0.925 | 4.1* |
| H81 | 0.807 | −0.145 | 0.828 | 3.7* |
| H121 | 0.931 | 0.445 | 0.750 | 4.2* |
| H111 | 1.059 | 0.409 | 0.840 | 4.7* |
| H191 | 0.860 | 0.041 | 1.014 | 5.3* |
| H151 | 0.830 | −0.626 | 0.906 | 5.7* |
| H181 | 0.719 | −0.054 | 1.053 | 6.5* |

TABLE 2-continued

Fractional Atomic Coordinates for the 2:1 L-phenylalanine compound 3 complex described in Example 4

| Atom | x | y | z | B(A2) |
|---|---|---|---|---|
| H161 | 0.695 | −0.712 | 0.946 | 6.4* |
| H311 | 0.325 | −0.066 | 0.530 | 3.2* |
| H331 | 0.354 | 0.135 | 0.692 | 3.5* |
| H332 | 0.313 | −0.159 | 0.698 | 3.5* |
| H351 | 0.398 | −0.451 | 0.770 | 4.0* |
| H381 | 0.637 | 0.159 | 0.819 | 4.5* |
| H391 | 0.512 | 0.226 | 0.728 | 3.9* |
| H361 | 0.524 | −0.522 | 0.859 | 5.1* |
| H371 | 0.643 | −0.220 | 0.884 | 5.0* |
| H431 | −0.032 | −0.256 | 0.663 | 3.8* |
| H432 | −0.008 | −0.562 | 0.653 | 3.8* |
| H411 | 0.128 | −0.460 | 0.534 | 3.4* |
| H451 | 0.149 | −0.711 | 0.695 | 4.3* |
| H491 | 0.051 | −0.026 | 0.747 | 4.7* |
| H481 | 0.175 | −0.006 | 0.841 | 5.1* |
| H461 | 0.271 | −0.687 | 0.789 | 5.2* |
| H471 | 0.285 | −0.326 | 0.861 | 5.6* |
| H411 | 0.128 | −0.460 | 0.534 | 3.4* |
| H412 | 0.179 | −0.404 | 0.607 | 3.4* |
| H413 | 0.115 | −0.638 | 0.593 | 3.4* |
| H311 | 0.325 | −0.066 | 0.530 | 3.2* |
| H312 | 0.263 | −0.029 | 0.584 | 3.2* |
| H313 | 0.333 | 0.179 | 0.574 | 3.2* |
| H201 | 0.556 | −0.447 | 0.982 | 10.3* |
| H202 | 0.611 | −0.665 | 1.035 | 10.3* |
| H211 | 0.529 | −0.407 | 1.084 | 12.8* |
| H212 | 0.642 | −0.377 | 1.114 | 12.8* |
| H213 | 0.587 | −0.159 | 1.061 | 12.8* |
| H02 | 0.657 | 0.576 | 0.763 | 4.4* |
| H03 | 0.559 | 0.600 | 0.637 | 4.2* |
| H04 | 0.613 | 0.157 | 0.539 | 4.0* |
| H06 | 0.911 | 0.120 | 0.559 | 4.3* |
| H2 | 0.592 | −0.256 | 0.554 | 6.8* |
| H1 | 0.575 | −0.135 | 0.476 | 6.8* |

Starred atoms were not refined.
Anisotropically refined atoms are given in the form of the isotropic equivalent displacement parameter defined as:
(4/3) * [a2 * B(1, 1) + b2 * B(2, 2) + c2 * B(3, 3) + ab(cos gamma) * B(1, 2) + ac(cos beta) * B(1, 3) + bc(cos alpha) * B(2, 3)]

TABLE 3

Fractional Atomic Coordinates for the 2:1 L-proline compound 3 complex described in Example 5

| Atom | x | y | z | B(A2) |
|---|---|---|---|---|
| O5 | −0.2661(3) | 0.0783(8) | 0.2681(1) | 3.14(8) |
| O2 | −0.0092(3) | 0.3427(9) | 0.2097(1) | 3.35(8) |
| O4 | −0.0727(3) | 0.3697(9) | 0.3675(1) | 3.76(9) |
| O3 | 0.0136(4) | 0.6044(9) | 0.2910(1) | 3.65(9) |
| O6 | −0.4235(4) | 0.241(1) | 0.3332(2) | 5.1(1) |
| C7 | −0.2367(5) | 0.022(1) | 0.1909(2) | 3.1(1) |
| C4 | −0.1439(5) | 0.349(1) | 0.3215(2) | 3.2(1) |
| C1 | −0.1673(4) | 0.084(1) | 0.2378(2) | 2.9(1) |
| C3 | −0.0405(5) | 0.375(1) | 0.2893(2) | 3.0(1) |

TABLE 3-continued

| | | | | |
|---|---|---|---|---|
| C2 | −0.1045(5) | 0.325(1) | 0.2402(2) | 2.8(1) |
| C8 | −0.1898(5) | −0.156(1) | 0.1665(2) | 3.6(1) |
| C5 | −0.2078(5) | 0.112(1) | 0.3156(2) | 3.1(1) |
| C13 | −0.2048(7) | −0.431(2) | 0.0997(2) | 6.3(2) |
| C6 | −0.3205(6) | 0.075(2) | 0.3435(2) | 4.7(2) |
| C14 | −0.0719(6) | −0.394(2) | 0.0828(2) | 4.4(1) |
| C9 | −0.2541(6) | −0.225(1) | 0.1235(2) | 4.6(1) |
| C12 | −0.3506(5) | 0.145(2) | 0.1714(2) | 4.3(1) |
| C10 | −0.3671(7) | −0.101(2) | 0.1049(2) | 5.2(2) |
| C19 | −0.0464(7) | −0.196(2) | 0.0589(2) | 4.9(2) |
| C17 | 0.1678(7) | −0.336(2) | 0.0484(3) | 5.6(2) |
| C18 | 0.0719(7) | −0.171(2) | 0.0419(2) | 5.2(2) |
| C15 | 0.0232(8) | −0.565(2) | 0.0891(2) | 5.3(2) |
| C11 | −0.4166(6) | 0.084(2) | 0.1286(2) | 4.8(2) |
| C16 | 0.1451(8) | −0.530(2) | 0.0724(3) | 6.0(2) |
| C20 | 0.2987(8) | −0.299(2) | 0.0264(4) | 7.9(3) |
| C21 | 0.3839(9) | −0.493(3) | 0.0259(3) | 8.3(3) |
| O43 | 0.1730(4) | 1.0009(9) | 0.2334(2) | 4.2(1) |
| O42 | 0.3494(4) | 1.1505(9) | 0.2771(2) | 4.3(1) |
| N41 | 0.2522(4) | 0.567(1) | 0.2421(2) | 3.3(1) |
| C42 | 0.2849(5) | 0.988(1) | 0.2570(2) | 3.0(1) |
| C43 | 0.4629(5) | 0.722(1) | 0.2348(2) | 4.2(2) |
| C41 | 0.3488(5) | 0.747(1) | 0.2625(2) | 3.0(1) |
| C44 | 0.3903(6) | 0.683(2) | 0.1861(2) | 5.0(2) |
| C45 | 0.2646(7) | 0.546(2) | 0.1916(2) | 4.6(2) |
| N31 | 0.2059(4) | 1.294(1) | 0.3985(2) | 3.7(1) |
| O33 | 0.1005(4) | 0.8816(9) | 0.3715(2) | 4.7(1) |
| O32 | 0.2939(5) | 0.7067(9) | 0.3728(2) | 5.1(1) |
| C32 | 0.2234(6) | 0.882(1) | 0.3780(2) | 3.3(1) |
| C31 | 0.2979(5) | 1.098(1) | 0.3930(2) | 3.2(1) |
| C34 | 0.3562(7) | 1.285(2) | 0.4680(3) | 5.7(2) |
| C35 | 0.2136(7) | 1.337(2) | 0.4498(2) | 5.5(2) |
| C33 | 0.3889(7) | 1.074(2) | 0.4392(2) | 5.3(2) |

Fractional Atomic Coordinates for BMS-356103P1 (cont.)

| | | | | |
|---|---|---|---|---|
| O300 | −0.0511(7) | 0.925(3) | 0.4452(3) | 14.1(3) |
| O400 | −0.1362(9) | 1.234(4) | 0.4822(3) | 16.6(4) |
| O100 | −0.4497(5) | 0.576(1) | 0.3940(2) | 8.1(2) |
| O200 | −0.2050(6) | 0.576(2) | 0.4295(2) | 11.9(3) |

Table of General Displacement Parameter Expressions for BMS-356103P1 - U's

| Name | U(1,1) | U(2,2) | U(3,3) | U(1,2) | U(1,3) | U(2,3) |
|---|---|---|---|---|---|---|
| O5 | 0.023(1) | 0.057(3) | 0.040(2) | −0.009(2) | 0.006(1) | −0.002(2) |
| O2 | 0.025(1) | 0.057(3) | 0.046(2) | −0.002(2) | 0.009(1) | 0.004(2) |
| O4 | 0.029(2) | 0.070(3) | 0.041(2) | −0.000(2) | −0.001(2) | −0.009(2) |
| O3 | 0.039(2) | 0.046(2) | 0.053(2) | −0.008(2) | 0.003(2) | −0.006(2) |
| O6 | 0.029(2) | 0.096(4) | 0.068(3) | 0.002(2) | 0.008(2) | −0.025(3) |
| C7 | 0.028(2) | 0.049(4) | 0.040(3) | −0.011(3) | 0.000(2) | 0.001(3) |
| C4 | 0.022(2) | 0.056(4) | 0.042(3) | −0.000(3) | −0.000(2) | −0.002(3) |
| C1 | 0.021(2) | 0.049(4) | 0.039(3) | −0.004(3) | 0.006(2) | 0.000(3) |
| C3 | 0.024(2) | 0.045(3) | 0.042(3) | −0.004(3) | −0.000(2) | −0.001(3) |
| C2 | 0.019(2) | 0.047(3) | 0.041(3) | −0.000(2) | 0.005(2) | −0.002(3) |
| C8 | 0.037(3) | 0.053(4) | 0.048(3) | −0.013(3) | 0.007(2) | −0.009(3) |
| C5 | 0.023(2) | 0.058(4) | 0.037(3) | −0.005(3) | 0.001(2) | −0.003(3) |
| C13 | 0.079(4) | 0.092(5) | 0.075(4) | −0.047(4) | 0.036(3) | −0.046(4) |
| C6 | 0.034(2) | 0.099(6) | 0.047(3) | −0.008(3) | 0.010(2) | −0.004(4) |
| C14 | 0.059(3) | 0.067(4) | 0.042(3) | −0.021(4) | 0.013(3) | −0.014(3) |
| C9 | 0.048(3) | 0.079(5) | 0.049(3) | −0.030(3) | 0.016(3) | −0.015(4) |
| C12 | 0.028(2) | 0.079(5) | 0.053(3) | −0.006(3) | −0.002(2) | 0.010(4) |
| C10 | 0.053(3) | 0.097(6) | 0.044(3) | −0.029(4) | 0.001(3) | −0.006(4) |
| C19 | 0.059(3) | 0.067(5) | 0.062(4) | −0.001(4) | 0.017(3) | −0.002(4) |
| C17 | 0.052(3) | 0.091(6) | 0.070(4) | −0.011(4) | 0.010(3) | −0.007(5) |
| C18 | 0.059(3) | 0.069(5) | 0.074(4) | −0.001(4) | 0.020(3) | −0.005(4) |
| C15 | 0.090(5) | 0.058(5) | 0.050(4) | −0.011(5) | 0.005(4) | 0.001(4) |
| C11 | 0.039(3) | 0.090(6) | 0.050(3) | −0.018(4) | −0.007(3) | 0.013(4) |
| C16 | 0.061(4) | 0.087(6) | 0.076(5) | 0.007(5) | −0.001(4) | −0.009(5) |
| C20 | 0.045(4) | 0.121(9) | 0.134(7) | −0.010(5) | 0.016(4) | −0.012(8) |
| C21 | 0.077(5) | 0.14(1) | 0.101(6) | 0.012(7) | 0.023(4) | −0.018(7) |
| O43 | 0.025(2) | 0.053(3) | 0.079(3) | 0.004(2) | −0.002(2) | 0.003(2) |
| O42 | 0.046(2) | 0.042(3) | 0.071(3) | 0.000(2) | −0.011(2) | −0.002(2) |
| N41 | 0.029(2) | 0.051(3) | 0.048(2) | −0.008(2) | 0.008(2) | −0.000(3) |
| C42 | 0.031(2) | 0.031(3) | 0.050(3) | 0.001(2) | 0.007(2) | 0.003(3) |
| C43 | 0.023(2) | 0.058(4) | 0.079(4) | −0.002(3) | 0.012(3) | −0.001(4) |
| C41 | 0.029(2) | 0.039(3) | 0.047(3) | −0.002(3) | 0.001(2) | 0.002(3) |
| C44 | 0.051(3) | 0.081(5) | 0.062(4) | −0.011(4) | 0.020(3) | −0.002(4) |
| C45 | 0.056(3) | 0.071(5) | 0.049(3) | −0.011(4) | 0.010(3) | −0.009(4) |
| N31 | 0.030(2) | 0.057(3) | 0.051(3) | 0.002(2) | −0.004(2) | −0.011(3) |

TABLE 3-continued

| | | | | | | |
|---|---|---|---|---|---|---|
| O33 | 0.040(2) | 0.055(3) | 0.080(3) | −0.012(2) | −0.004(2) | −0.014(3) |
| O32 | 0.062(3) | 0.049(3) | 0.085(3) | −0.001(3) | 0.017(2) | −0.002(3) |
| C32 | 0.045(3) | 0.036(3) | 0.044(3) | 0.003(3) | 0.004(2) | −0.001(3) |
| C31 | 0.032(2) | 0.040(3) | 0.051(3) | 0.003(3) | 0.007(2) | −0.004(3) |
| C34 | 0.062(4) | 0.095(6) | 0.054(4) | −0.008(5) | −0.009(3) | −0.009(5) |
| C35 | 0.057(3) | 0.096(6) | 0.058(3) | −0.009(4) | 0.018(3) | −0.028(4) |
| C33 | 0.053(3) | 0.068(5) | 0.070(4) | 0.006(4) | −0.023(3) | −0.006(4) |
| O300 | 0.109(4) | 0.33(1) | 0.093(4) | −0.097(7) | 0.022(4) | −0.033(7) |
| O400 | 0.147(7) | 0.35(2) | 0.131(6) | −0.00(1) | 0.029(5) | 0.107(8) |
| O100 | 0.064(3) | 0.112(5) | 0.133(4) | 0.001(4) | 0.023(3) | −0.053(4) |
| O200 | 0.065(3) | 0.29(1) | 0.097(4) | 0.027(5) | 0.006(3) | −0.088(5) |

The form of the anisotropic displacement parameter is:
exp [−2PI2{h2a2U(1,1) + k2b2U(2,2) + 12c2U(3,3) + 2hkabU(1,2) + 2hlacU(1,3) + 2klbcU(2,3)}] where a, b, and c are reciprocal lattice constants.

Hydrogen Atoms for BMS-356103P1 (not refined)

| Atom | x | y | z | B(A2) |
|---|---|---|---|---|
| H11 | −0.091 | −0.037 | 0.249 | 3.9* |
| H61 | −0.283 | 0.082 | 0.379 | 5.6* |
| H62 | −0.364 | −0.094 | 0.335 | 5.6* |
| H51 | −0.132 | −0.012 | 0.325 | 4.2* |
| H41 | −0.218 | 0.492 | 0.315 | 4.2* |
| H31 | 0.040 | 0.260 | 0.300 | 4.1* |
| H21 | −0.182 | 0.461 | 0.230 | 3.8* |
| H81 | −0.103 | −0.247 | 0.183 | 4.6* |
| H121 | −0.389 | 0.294 | 0.191 | 5.4* |
| H111 | −0.502 | 0.185 | 0.112 | 5.9* |
| H101 | −0.419 | −0.149 | 0.071 | 6.2* |
| H131 | −0.280 | −0.461 | 0.069 | 7.0* |
| H132 | −0.199 | −0.569 | 0.122 | 7.0* |
| H191 | −0.120 | −0.052 | 0.053 | 5.8* |
| H181 | 0.089 | −0.014 | 0.023 | 6.1* |
| H161 | 0.223 | −0.655 | 0.079 | 7.0* |
| H151 | 0.010 | −0.719 | 0.107 | 6.3* |
| H451 | 0.278 | 0.375 | 0.182 | 5.6* |
| H452 | 0.179 | 0.626 | 0.171 | 5.6* |
| H351 | 0.184 | 1.516 | 0.458 | 6.5* |
| H352 | 0.147 | 1.221 | 0.465 | 6.5* |
| H311 | 0.359 | 1.155 | 0.367 | 4.3* |
| H312 | 0.112 | 1.253 | 0.385 | 4.7* |
| H431 | 0.525 | 0.880 | 0.237 | 5.1* |
| H432 | 0.524 | 0.577 | 0.246 | 5.1* |
| H441 | 0.361 | 0.859 | 0.169 | 5.9* |
| H442 | 0.449 | 0.599 | 0.164 | 5.9* |
| H341 | 0.417 | 1.438 | 0.460 | 6.8* |
| H342 | 0.372 | 1.258 | 0.504 | 6.8* |
| H331 | 0.363 | 0.922 | 0.457 | 6.6* |
| H332 | 0.492 | 1.075 | 0.437 | 6.6* |
| H06 | −0.500 | 0.179 | 0.312 | 6.1* |
| H201 | 0.271 | −0.237 | −0.010 | 8.7* |
| H202 | 0.358 | −0.154 | 0.044 | 8.7* |
| H03 | 0.021 | 0.674 | 0.323 | 4.7* |
| H411 | 0.379 | 0.716 | 0.299 | 4.2* |
| H412 | 0.273 | 0.421 | 0.258 | 4.3* |
| H002 | −0.441 | 0.458 | 0.371 | 8.9* |
| H004 | −0.145 | 0.721 | 0.437 | 13.0* |
| H001 | −0.544 | 0.638 | 0.389 | 8.9* |
| H411 | 0.379 | 0.716 | 0.299 | 4.2* |
| H311 | 0.359 | 1.155 | 0.367 | 4.3* |
| H02 | 0.060 | 0.225 | 0.218 | 4.3* |
| H04 | −0.130 | 0.455 | 0.387 | 4.8* |
| H211 | 0.477 | −0.450 | 0.013 | 9.3* |
| H210 | 0.412 | −0.559 | 0.061 | 9.3* |
| H213 | 0.335 | −0.631 | 0.005 | 9.3* |
| H003 | −0.294 | 0.634 | 0.416 | 13.0* |
| H006 | −0.066 | 1.109 | 0.451 | 14.0* |
| H005 | 0.001 | 0.922 | 0.420 | 14.0* |
| H008 | −0.068 | 1.311 | 0.507 | 17.3* |
| H007 | −0.166 | 1.365 | 0.460 | 17.3* |

Starred atoms were not refined.
Anisotropically refined atoms are given in the form of the isotropic equivalent displacement parameter defined as:
(4/3) * [a2 * B(1, 1) + b2 * B(2, 2) + c2 * B(3, 3) + ab(cos gamma) * B(1, 2) + ac(cos beta) * B(1, 3) + bc(cos alpha) * B(2, 3)]

TABLE 4

Fractional Atomic Coordinates for the 1:1 complex of
L-proline and compound 3 described in Example 6

Fractional Atomic Coordinates for
BMS-356103P3

| atom | X | Y | Z | U11*10e2 | U22*10e2 | U33*10e2 | U12*10e2 | U13*10e2 | U23*10e2 |
|---|---|---|---|---|---|---|---|---|---|
| O2 | 0.1436(14) | 0.6331(7) | 0.1498(2) | 130(11) | 136(9) | 215(10) | 26(9) | −34(8) | −15(9) |
| O3 | −0.1155(17) | 0.6081(16) | 0.2052(2) | 153(15) | 666(35) | 222(13) | 171(20) | −39(9 ) | −231(18) |
| O4 | 0.0896(16) | 0.4381(21) | 0.2547(2) | 178(19) | 1164(60) | 99(10) | 286(27) | −1(8) | −119(19) |
| O5 | 0.4018(12) | 0.3352(6) | 0.1861(1) | 158(11) | 140(8) | 65(6) | 0(7) | 22(6) | 31(6) |
| O6 | 0.2656(21) | 0.1329(13) | 0.2290(2) | 247(18) | 483(25) | 197(12) | −103(20) | 19(12) | 213(15) |
| C1 | 0.3929(18) | 0.4551(9) | 0.1674(2) | 104(16) | 139(12) | 92(10) | 2(12) | −11(10) | −12(9) |
| C2 | 0.1595(18) | 0.5212(10) | 0.1698(2) | 75(15) | 160(14) | 122(12) | 7(12) | −22(9) | −17(11) |
| C3 | 0.1116(22) | 0.5506(18) | 0.2028(3) | 126(20) | 436(32) | 126(16) | 170(22) | −69(13) | −171(19) |
| C4 | 0.1298(23) | 0.4287(24) | 0.2224(2) | 87(19) | 636(47) | 46(11) | 59(24) | 26(10) | −61(19) |
| C5 | 0.3702(24) | 0.3674(13) | 0.2189(2) | 150(20) | 311(22) | 57(10) | 17(18) | 28(10) | 24(12) |
| C6 | 0.4326(28) | 0.2345(19) | 0.2360(3) | 217(25) | 399(30) | 118(13) | −88(27) | −11(14) | 76(18) |
| C7 | 0.4539(19) | 0.4164(8) | 0.1339(2) | 106(14) | 72(9) | 81(10) | 20(10) | 0(11) | −3(9) |
| C8 | 0.6364(18) | 0.4776(9) | 0.1195(2) | 97(14) | 126(11) | 98(11) | 48(11) | 20(10) | 43(9) |
| C9 | 0.6949(22) | 0.4470(11) | 0.0889(2) | 120(17) | 150(14) | 125(14) | 66(14) | 27(13) | 46(11) |
| C10 | 0.5596(25) | 0.3488(13) | 0.0736(2) | 188(21) | 203(17) | 47(10) | 100(16) | 52(13) | 40(12) |
| C11 | 0.3860(26) | 0.2875(11) | 0.0882(2) | 216(24) | 163(14) | 86(13) | 47(17) | −24(13) | −31(10) |
| C12 | 0.3301(19) | 0.3179(10) | 0.1191(2) | 132(15) | 134(12) | 98(12) | 6(13) | 0(11) | 18(10) |
| C13 | 0.8967(22) | 0.5142(12) | 0.0740(2) | 152(20) | 210(17) | 168(13) | 95(16) | 61(13) | 101(13) |
| C14 | 0.8456(20) | 0.6513(10) | 0.0597(2) | 114(16) | 158(13) | 81(9) | 43(14) | 26(10) | 36(20) |
| C15 | 0.6446(24) | 0.7243(12) | 0.0654(2) | 137(19) | 178(17) | 137(13) | 43(16) | 9(12) | 59(12) |
| C16 | 0.6132(21) | 0.8509(11) | 0.0524(2) | 115(17) | 155(15) | 137(13) | 39(14) | −20(15) | 2(12) |
| C17 | 0.7781(28) | 0.9048(12) | 0.0332(2) | 169(21) | 167(16) | 144(14) | −15(17) | −33(14) | 22(13) |
| C18 | 0.9626(26) | 0.8305(13) | 0.0260(3) | 141(22) | 139(15) | 191(17) | 7(16) | 5(14) | 20(14) |
| C19 | 0.9997(23) | 0.7087(12) | 0.0405(3) | 149(19) | 167(17) | 168(15) | −1(15) | 16(15) | 34(13) |
| C20 | 0.7286(37) | 1.0466(12) | 0.0186(3) | 334(33) | 93(15) | 350(26) | −61(20) | −94(24) | 57(16) |
| O7 | 0.5116(23) | 0.7913(12) | 0.1571(4) | 201(19) | 142(12) | 607(31) | −71(21) | −66(18) | 18(16) |
| O8 | 0.3530(22) | 0.9532(13) | 0.1847(3) | 117(16) | 238(16) | 435(23) | −34(14) | −79(14) | 33(15) |
| N21 | 0.9396(20) | 0.8845(10) | 0.1581(4) | 105(16) | 139(13) | 469(30) | 35(12) | −90(16) | −41(16) |
| C22 | 0.7565(21) | 0.9683(10) | 0.1744(2) | 116(18) | 138(14) | 191(15) | −39(14) | −62(13) | 53(12) |
| C23 | 0.7666(23) | 1.0971(10) | 0.1572(2) | 167(20) | 131(13) | 181(15) | 1(13) | −53(13) | 23(12) |
| C24 | 0.7989(26) | 1.0509(13) | 0.1240(4) | 205(22) | 178(16) | 190(16) | 17(17) | −42(15) | −3(13) |
| C25 | 0.9691(29) | 0.9386(17) | 0.1249(4) | 250(28) | 264(23) | 236(21) | 89(23) | −74(20) | −54(20) |
| C26 | 0.5235(36) | 0.8940(19) | 0.1718(5) | 153(31) | 162(23) | 368(30) | −39(23) | −133(24) | 102(21) |
| C21 | 0.9289(38) | 1.1279(13) | 0.0195(4) | 360(39) | 124(17) | 372(30) | 14(23) | 105(26) | 12(17) |

| atom | X | Y | Z | UX10E2 |
|---|---|---|---|---|
| H02 | 0.2877(0) | 0.6900(0) | 0.1535(0) | 9.78(0) |
| H03 | −0.1655(0) | 0.6145(0) | 0.2274(0) | 18.59(0) |
| H04 | −0.0347(0) | 0.5093(0) | 0.2585(0) | 25.31(0) |
| H06 | 0.3278(0) | 0.0727(0) | 0.2122(0) | 17.32(0) |
| H11 | 0.5248(0) | 0.5259(0) | 0.1757(0) | 6.86(0) |
| H21 | 0.0255(0) | 0.4482(0) | 0.1626(0) | 7.28(0) |
| H31 | 0.2412(0) | 0.6192(0) | 0.2116(0) | 12.91(0) |
| H41 | 0.0004(0) | 0.3584(0) | 0.2134(0) | 14.84(0) |
| H51 | 0.4986(0) | 0.4373(0) | 0.2268(0) | 10.36(0) |
| H61 | 0.4426(0) | 0.2519(0) | 0.2601(0) | 13.44(0) |
| H62 | 0.6037(0) | 0.2036(0) | 0.2272(0) | 13.44(0) |
| H81 | 0.7419(0) | 0.5336(0) | 0.1318(0) | 6.67(0) |
| H101 | 0.5942(0) | 0.3256(0) | 0.0497(0) | 9.05(0) |
| H111 | 0.2868(0) | 0.2135(0) | 0.0754(0) | 9.82(0) |
| H121 | 0.1916(0) | 0.2629(0) | 0.1314(0) | 7.50(0) |
| H131 | 1.0323(0) | 0.5262(0) | 0.0915(0) | 9.92(0) |
| H132 | 0.9629(0) | 0.4487(0) | 0.0559(0) | 9.92(0) |
| H151 | 0.5061(0) | 0.6809(0) | 0.0803(0) | 9.63(0) |
| H161 | 0.4546(0) | 0.9090(0) | 0.0576(0) | 8.68(0) |
| H181 | 1.0815(0) | 0.8639(0) | 0.0078(0) | 10.98(0) |
| H191 | 1.1591(0) | 0.6529(0) | 0.0354(0) | 9.96(0) |
| H201 | 0.6783(0) | 1.0354(0) | −0.0058(0) | 14.60(0) |
| H202 | 0.5853(0) | 1.0950(0) | 0.0306(0) | 14.60(0) |
| H211 | 1.0919(0) | 0.8918(0) | 0.1702(0) | 12.10(0) |
| H221 | 0.7949(0) | 0.9804(0) | 0.1986(0) | 9.04(0) |
| H231 | 0.6013(0) | 1.1526(0) | 0.1599(0) | 9.68(0) |
| H232 | 0.9053(0) | 1.1599(0) | 0.1651(0) | 9.68(0) |
| H241 | 0.6351(0) | 1.0181(0) | 0.1140(0) | 10.91(0) |
| H242 | 0.8670(0) | 1.1318(0) | 0.1098(0) | 10.91(0) |
| H251 | 1.1440(0) | 0.9723(0) | 0.1206(0) | 14.31(0) |
| H252 | 0.9248(0) | 0.8621(0) | 0.1078(0) | 14.31(0) |

TABLE 4-continued

Fractional Atomic Coordinates for the 1:1 complex of
L-proline and compound 3 described in Example 6

| H211 | 0.9036(0) | 1.2243(0) | 0.0106(0) | 14.36(0) |
| --- | --- | --- | --- | --- |
| H212 | 0.9816(0) | 1.1383(0) | 0.0448(0) | 14.36(0) |
| H213 | 1.0745(0) | 1.0786(0) | 0.0083(0) | 14.36(0) |
| H212 | 0.8930(0) | 0.7875(0) | 0.1582(0) | 12.10(0) |

What is claimed:

1. Crystalline complexes between either (D) or (L) enantiomers of natural amino acids and compounds of formula I

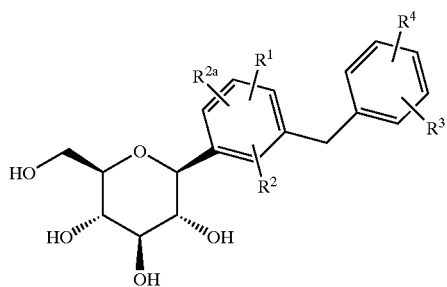

wherein $R^1$, $R^2$ and $R^{2a}$ are independently hydrogen, OH, $OR^5$, alkyl, —$OCHF_2$, —$OCF_3$, —$SR^{5a}$ or halogen;

$R^3$ and $R^4$ are independently hydrogen, OH, $OR^{5b}$, alkyl, cycloalkyl, $CF_3$, —$OCHF_2$, —$OCF_3$, halogen, —$CONR^6R^{6a}$, —$CO_2R^{5c}$, —$CO_2H$, —$COR^{6b}$, —CH(OH)$R^{6c}$, —CH($OR^{5d}$)$R^{6d}$, —CN, —$NHCOR^{5e}$, —$NHSO_2R^{5f}$, —$NHSO_2$Aryl, —$SR^{5g}$, —$SOR^{5h}$, —$SO_2R^{5i}$, or a five, six or seven membered heterocycle which may contain 1 to 4 heteroatoms in the ring which are N, O, S, SO, and/or $SO_2$, or $R^3$ and $R^4$ together with the carbons to which they are attached form an annelated five, six or seven membered carbocycle or heterocycle which may contain 1 to 4 heteroatoms in the ring which are N, O, S, SO, $SO_2$;

$R^5$, $R^{5a}$, $R^{5b}$, $R^{5c}$, $R^{5d}$, $R^{5e}$, $R^{5f}$, $R^{5g}$, $R^{5h}$ and $R^{5i}$ are independently alkyl;

$R^6$, $R^{6a}$, $R^{6b}$, $R^{6c}$ and $R^d$ are independently hydrogen, alkyl, aryl, alkylaryl or cycloalkyl, or $R^6$ and $R^{6a}$ together with the nitrogen to which they are attached form an annelated five, six or seven membered heterocycle which may contain 1 to 4 heteroatoms in the ring which are N, O, S, SO, and/or $SO_2$.

2. Complexes of either the (D) or (L) enantiomer of natural amino acids with compounds as defined in claim 1 where $R^1$ is hydrogen, alkoxy, halogen or lower alkyl; and $R^4$ is lower alkyl, $R^{5a}O$, —$OCHF_2$, —$SR^{5e}$, —$S(O)R^{5e}$, or —$S(O_2)R^{5e}$.

3. Crystalline 1:1 or 2:1 complexes of L-phenylalanine or L-proline or D-phenylalanine with compounds as defined in claim 2 wherein $R^1$ is hydrogen or methyl and $R^4$ is 4-$C_2H_5$, —$OCHF_2$, or —SMe.

4. Complexes of either the (D) or (L) enantiomer of natural amino acids with with compounds as defined in claim 2 having the structure

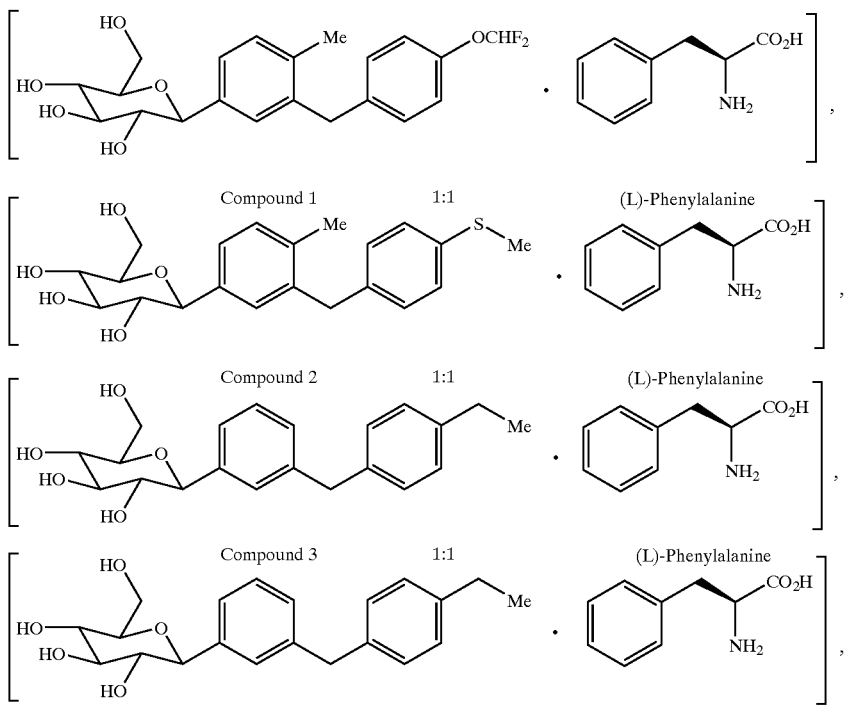

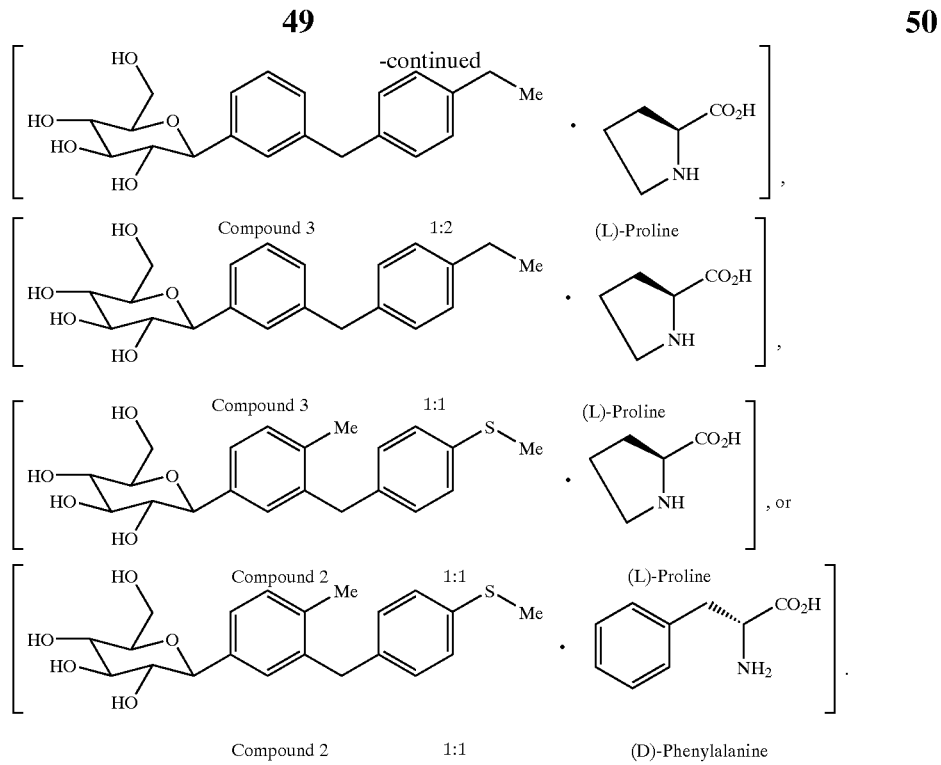

5. Crystalline 1:1 or 2:1 complexes of L-phenylalanine or L-proline or D-phenylalanine with compounds as defined in claim 1 having the structure

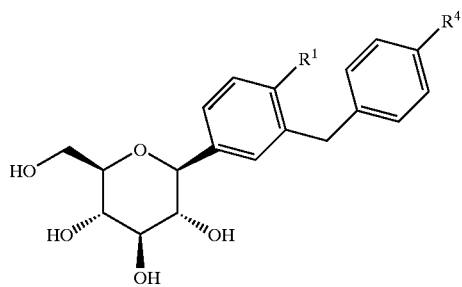

where $R^1$ is hydrogen, alkoxy, halogen or lower alkyl; and $R^4$ is lower alkyl, $R^{5a}O$, —$OCHF_2$, —$SR^{5e}$, —$S(O)R^{5e}$, or —$S(O_2)R^{5e}$.

6. A pharmaceutical composition comprising a complex as defined in claim 1 and a pharmaceutically acceptable carrier therefor.

7. A pharmaceutical combination comprising a complex of either the (D) or (L) enantiomer of natural amino acids with a compound as defined in claim 1 and an antidiabetic agent other than an SGLT2 inhibitor, an agent for treating the complications of diabetes, an anti-obesity agent, an antihypertensive agent, an antiplatelet agent, an antiatherosclerotic agent, and/or lipid-lowering agent.

8. The pharmaceutical combination as defined in claim 7 comprising said compound complexed with either the (D) or (L) enantiomer of natural amino acids and an antidiabetic agent.

9. The combination as defined in claim 8 wherein the complexes of either the (D) or (L) enantiomer of natural amino acids with a compound is present in a weight ratio to the antidiabetic agent within the range from about 0.01 to about 300:1.

10. The combination as defined in claim 7 wherein the anti-obesity agent is a beta 3 adrenergic agonist, a lipase inhibitor, a serotonin reuptake inhibitor, a thyroid receptor beta compound, and/or an anorectic agent.

11. The combination as defined in claim 10 wherein the anti-obesity agent is orlistat, sibutramine, topiramate, axokine, dexamphetamine, phentermine, phenylpropanolamine, and/or mazindol.

12. The combination as defined in claim 7 wherein the lipid lowering agent is an MTP inhibitor, an HMG CoA reductase inhibitor, a squalene synthetase inhibitor, a fibric acid derivative, an upregulator of LDL receptor activity, a lipoxygenase inhibitor, or an ACAT inhibitor.

13. The combination as defined in claim 12 wherein the lipid lowering agent is pravastatin, lovastatin, simvastatin, atorvastatin, cerivastatin, fluvastatin, nisvastatin, visastatin, atavastatin, rosuvastatin, fenofibrate, gemfibrozil, clofibrate, or avasimibe.

14. The combination as defined in claim 12 wherein the complexes are present in a weight ratio to the lipid-lowering agent within the range from about 0.01 to about 300:1.

15. The combination as defined in claim 8 wherein the antidiabetic agent is selected from 1, 2, 3 or more of the group of: a biguanide, a sulfonyl urea, a glucosidase inhibitor, a PPAR γ agonist, a PPAR α/γ dual agonist, an aP2 inhibitor, a DP4 inhibitor, an insulin sensitizer, a glucagon-like peptide-1 (GLP-1), insulin, a meglitinide, a PTP1B inhibitor, a glycogen phosphorylase inhibitor, a glucoser-6-phosphatase inhibitor.

16. The combination as defined in claim 15 wherein the antidiabetic agent is selected from 1, 2, 3 or more of the group of: metformin, glyburide, glimepiride, glipyride, glipizide, chlorpropamide, gliclazide, acarbose, miglitol, pioglitazone, troglitazone, rosiglitazone, insulin, and isaglitazone, repaglinide, nateglinide.

17. A method for treating or delaying the progression or onset of diabetes, diabetic retinopathy, diabetic neuropathy, diabetic nephropathy, delayed wound healing, insulin resistance, hyperglycemia, hyperinsulinemia, elevated blood levels of fatty acids or glycerol, hyperlipidemia, obesity, hypertriglyceridemia, Syndrome X, diabetic complications, atherosclerosis or hypertension, or for increasing high density lipoprotein levels, which comprises administering to a mammalian species in need of treatment a therapeutically effective amount of a natural amino acid complex as defined in claim 1.

18. The method as defined in claim 17 where compounds of Formula (I) have the structure

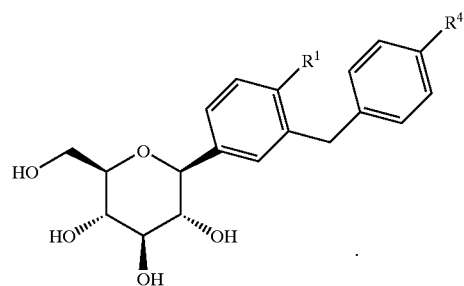

19. A method for treating type II diabetes which comprises administering to a mammalian species in need of treatment a therapeutically effective amount of a complex as defined in claim 1 alone or in combination with another antidiabetic agent, an agent for treating the complications of diabetes, an anti-obesity agent, an antihypertensive agent, an antiplatelet agent, an anti-atherosclerotic agent a hypolipidemic agent.

* * * * *